United States Patent [19]

Kobori et al.

[11] Patent Number: 5,073,551

[45] Date of Patent: Dec. 17, 1991

[54] CEPHALOSPORIN COMPOUNDS

[75] Inventors: Takeo Kobori, Atsugi; Daiei Tunemoto, Zama, both of Japan

[73] Assignee: Sagami Chemical Research Center, Tokyo, Japan

[21] Appl. No.: 334,206

[22] Filed: Mar. 24, 1989

[30] Foreign Application Priority Data

| Mar. 30, 1988 | [JP] | Japan | 63-74676 |
| Apr. 6, 1988 | [JP] | Japan | 63-83014 |
| Aug. 25, 1988 | [JP] | Japan | 63-209433 |
| Aug. 25, 1988 | [JP] | Japan | 63-209434 |

[51] Int. Cl.$^5$ .................. C07D 501/36; A61K 31/545
[52] U.S. Cl. .................... 514/206; 540/226; 540/227
[58] Field of Search .............. 514/206; 540/226, 222, 540/225, 227

[56] References Cited

U.S. PATENT DOCUMENTS

| 4,520,193 | 5/1985 | Berger et al. | 540/227 |
| 4,839,350 | 6/1989 | Atsumi et al. | 540/227 |
| 4,918,068 | 4/1990 | Yamamoto et al. | 540/227 |
| 4,927,922 | 5/1990 | Lee et al. | 540/227 |

FOREIGN PATENT DOCUMENTS 0103264 3/1984 European Pat. Off. .
0175610 3/1986 European Pat. Off. .

OTHER PUBLICATIONS

Sankyo Co., Ltd., Chemical Abstracts, vol. 94, No. 19, May 11, 1981, Abstract No. 156948s.

*Primary Examiner*—Nicholas S. Rizzo
*Attorney, Agent, or Firm*—Wenderoth, Lind & Ponack

[57] ABSTRACT

Cephalosporin compounds represented by the general formula in which $R^1$ is a hydrogen atom or a protective group for the amino group,
$R^2$ is a hydrogen atom or a protective group for the hydroxyl group,
$R^3$ is a hydrogen atom, a salt-forming cation or a protective group for the carboxyl group, and
$R^4$ is a hydrogen atom, a halogen atom or a lower alkyl group, and their pharmacologically acceptable salts, process for their production and use of the same compounds as medicaments, particularly as antibiotic agents.

11 Claims, No Drawings

CEPHALOSPORIN COMPOUNDS

The present invention relates to novel cephalosporin compounds and more particularly, to cephalosporin compounds represented by the general formula

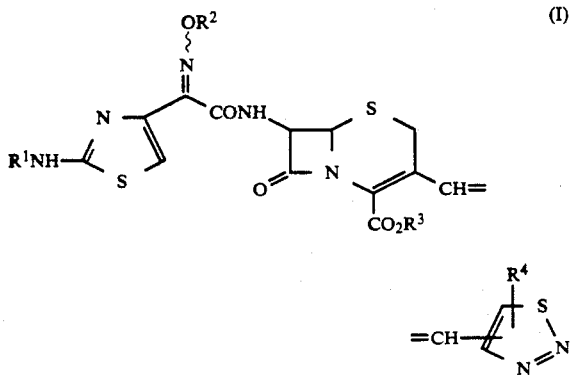

in which $R^1$ is a hydrogen atom or a protective group for the amino group, $R^2$ is a hydrogen atom or a protective group for the hydroxyl group, $R^3$ is a hydrogen atom, a salt-forming cation or a protective group for the carboxyl group, and $R^4$ is a hydrogen atom, a halogen atom or a lower alkyl group, and their pharmacologically acceptable salts, process for their production and use of the same compounds as medicaments, particularly as antibiotic agents.

Heretofore, in developments of cephalosporin derivatives, the type of chemical modification in their 3-position is well known to greatly affect their physiological activity, and various 3-modified derivatives have been proposed. Of these proposals, cephalosporin derivatives are already known which contain in the 3-position a tetrazole-substituted vinyl group (refer to Japanese Laid-open Patent Application No. 124790/1980, C.A. 94. 156948s), pyridyl- or pyridazinyl-substituted vinyl group (refer to Japanese Laid-open Patent Application No. 76088/1984, European Patent 103264, U.S. Pat. No. 4546101), phenyl, furyl- or thiazole-substituted vinyl group (refer to Japanese Laid-open Patent Application No. 178991/1986, European Patent 175610) and the like.

However, cephalosporin compounds containing in the 3-position a substituted or unsubstituted 1,2,3-thiadiazolylvinyl group as is the case with the compounds of said formula (I) which the present invention provides have never been proposed.

The instant inventors accomplished the present invention with the finding that novel cephalosporin compounds represented by said formula (I) show superior antimicrobial activity on a wide range of pathogenic microorganisms, including gram-positive bacteria and gram-negative bacteria.

Thus, the primary object of the present invention is to provide, as novel compounds, cephalosporin compounds represented by said general formula (I).

Another object of the present invention is to provide a process for production of cephalosporin compounds of said formula (I).

Still another object of the present invention is to provide medicaments, particularly antibacterial agents, containing cephalosporin compounds of said formula (I).

Other objects and advantages with the present invention will be self-explanatory from following detailed description.

By the term "lower" used in the instant specification is meant that the number of carbon atoms contained in the compound to which this term is affixed is 6 carbons or less, preferably 4 carbons or less.

In this general formula (I), the "protective group for the amino group" may be a usual optional amino protective group capable of readily splitting off by hydrolysis or hydrogenolysis. For example, there are cited an esterified carboxyl group, such as ethoxycarbonyl, tert-butoxycarbonyl, isobornyloxycarbonyl, trichloroethoxycarbonyl, phenoxycarbonyl, benzyloxycarbonyl and the like; aliphatic acyl group, such as formyl, acetyl, valeryl, capryl, n-decanoyl, acryloyl, pivaloyl, chloroacetyl, bromoacetyl, camphasulfonyl, methanesulfonyl and the like; aromatic acyl group, such as phthaloyl, benzoyl, chlorobenzoyl, p-nitrobenzoyl, p-tert-butylbenzoyl, toluoyl, naphthoyl and the like; aromatic-aliphatic acyl group, such as phenylacetyl, phenoxyacetyl and the like; aralkyl group, such as benzyl, benzhydryl, trityl and the like; silyl group, such as trimethylsilyl, dimethylsilyl and the like; carbamoyl group, such as methylcarbamoyl, phenylcarbamoyl, naphthylcarbamoyl and the like, and corresponding thiocarbamoyl groups; and so forth. Of these, preferable are tert-butoxycarbonyl, benzyloxycarbonyl, formyl, chloroacetyl, trityl, trimethylsilyl, dimethylsilyl and the like, and more preferable are tert-butoxycarbonyl, formyl, chloroacetyl, and trityl.

As the "protective group for the hydroxyl group" particularly aliphatic, aromatic, heterocyclic, aromatic-aliphatic and heterocyclic-aliphatic acyl groups are suitable and these acyl groups will be explained in more detail hereinafter.

(a) As the aliphatic acyl group there are cited saturated or unsaturated, acyclic or cyclic acyl groups, such as lower alkanoyl group, such as formyl, acetyl, propionyl, butyryl, pivaloyl, hexanoyl and the like; lower alkanesulfonyl group, such as mesyl, ethane-sulfonyl, propanesulfonyl and the like; lower alkoxycarbonyl group, such as methoxycarbonyl, ethoxycarbonyl, propoxycarbonyl, butoxycarbonyl, tertiary butoxycarbonyl and the like; lower alkenoyl group, such as acryloyl, methacryloyl, crotonoyl and the like; ($C_3$–$C_7$)-cycloalcarbonyl group, such as cyclohexanecarbonyl and the like; amidino group and so forth.

(b) As the aromatic acyl group there are cited an aroyl group, such as benzoyl, toluoyl, xyloyl and the like; and allenesulfonyl group, such as benzenesulfonyl, tosyl and the like.

(c) As the heterocyclic acyl group there are cited a heterocyclic carbonyl group, such as furoyl, thenoyl, nicotinoyl, isonicotinoyl, thiazolylcarbonyl, thiadiazolylcarbonyl, tetrazolylcarbonyl and the like, and so forth.

As the aromatic-aliphatic acyl group there are cited an ar-lower alkanoyl group, such as phenyl-lower alkanoyl group, such as phenylacetyl, phenylpropionyl, phenylhexanoyl and the like; ar-lower alkoxycarbonyl group, such as phenyl-lower alkoxycarbonyl group, such as benzyloxycarbonyl, phenethloxycarbonyl and the like; phenoxy-lower alkanoyl group, such as phenoxyacetyl, phenoxypropionyl and the like, and so forth.

(d) As the heterocyclic-aliphatic acyl group there are cited thienylacetyl, imidazolylacetyl, furylacetyl, tetrazolylacetyl, thiazolylacetyl, thiadiazolylacetyl, thienypropionyl, thiadiazolylpropionyl and the like.

These acyl groups may suitably be substituted by one or more substituents chosen from a lower alkyl group, such as methyl, ethyl, propyl, isopropyl, butyl, pentyl, hexyl and the like; lower alkoxy group, such as methoxy, ethoxy, propoxy, isopropoxy, butoxy, pentyloxy, hexyloxy and the like; lower alkylthio group, such as methylthio, ethylthio, propylthio, isopropylthio, butylthio, pentylthio, hexylthio and the like; nitro group and so forth, and as a preferable acyl group containing such substituents there are cited a mono-, di- or tri-halo-lower alkanoyl group, such as chloroacetyl, bromoacetyl, dichloroacetyl, trifluoroacetyl and the like; mono-, di- or tri-halo-lower alkoxycarbonyl group, such as chloromethoxycarbonyl, dichloromethoxycarbonyl, 2,2,2-trichloroethoxycarbonyl and the like; nitro-, halo- or lower alkoxy-substituted phenyl-lower alkoxycarbonyl group, such as nitrobenzyloxycarbonyl, chlorobenzyloxycarbonyl, methoxybenzyloxycarbonyl and the like, and so forth.

Further, as the protective group for the hydroxyl group there are cited an aralkyl group, such as benzyl, benzhydryl, trityl and the like; lower alkoxy-lower alkyl group, such as 1-methyl-1-methoxyethyl, methoxypropyl and the like; tetrahydropyranyl and the like.

Of the aforesaid protective groups for the hydroxy group, as preferred ones there are cited trityl, 1-methyl-1-methoxyethyl and tetrahydropyranyl, and more preferably trityl and 1-methyl-1-methoxyethyl.

As the "protective group for the carboxyl group" there may be used optional protective groups known per se which are generally used in chemical fields of penicillin, cephalosporin, and the like, and for example, ester residues are cited. More specifically, there are cited a lower alkyl group, such as methyl, ethyl, propyl, isopropyl, butyl, isobutyl, tert-butyl, pentyl, tert-pentyl, hexyl and the like; lower alkenyl group, such as vinyl, allyl and the like; lower alkynyl group, such as ethynyl, propyl and the like; lower alkoxy-lower alkyl group; such as methoxymethyl ethoxymethyl, isopropoxymethyl, 1-methoxyethyl, 1-ethoxyethyl and the like; lower alkylthio-lower alkyl group, such as methylthiomethyl, ethylthiomethyl, ethylthioethyl, isopropylthiomethyl and the like; carboxy-substituted lower alkyl group, such as carboxymethyl, 2-carboxyethyl, 3-carboxypropyl and the like; protected carboxy substituted lower alkyl group, such as lower alkoxycarbonyl substituted-lower alkyl group, such as tert-butoxycarbonylmethyl, 2-tert-butoxycarbonylethyl, 3-tert-butyoxcarbonylpropyl and the like; mono-, di- or tri-halo lower alkyl group, such as 2-iodoethyl, 2,2,2-trichloroethyl and the like; lower alkanoyloxy-lower alkyl group, such as acetoxymethyl, propionyloxymethyl, butyryloxymethyl, valeryloxymethyl, pivaloyloxymethyl, hexanoyloxymethyl, 1- or 2-acetoxyethyl, 1-, 2- or 3-acetoxypropyl, 1-, 2-, 3- or 4-acetoxypropyl, 1- or 2-propionyloxyethyl, 1-, 2- or 3-propionyloxypropyl, 1- or 2-butyryloxyethyl, 1- or 2-isobutyryloxyethyl, 1- or 2-pivaloyloxyethyl, 1- or 2-hexanoyloxyethyl, isobutyryloxymethyl, 2-ethylbutyryloxymethyl, 3,3-dimethylbutyryloxymethyl, 1- or 2-pentanoyloxyethyl and the like; higher alkanoyloxy-lower alkyl group, such as heptanoyloxymethyl, octanoyloxymethyl, nonanoyloxymethyl, decanoyloxymethyl, undecanoyloxymethyl, lauroloxymethyl, tridecanoyloxymethyl, myristolyloxymethyl, pentadecanoyloxymethyl, palmitolyoxymethyl, heptadecanoyloxymethyl, stearoyloxymethyl, nonadecanoyloxymethyl, eicosanoyloxymethyl, 1- or 2-heptanoyloxyethyl, 1- or 2-octanoyloxyethyl, 1- or 2-nonanoyloxyethyl, 1- or 2-decanoyloxyethyl, 1- or 2-undecanoyloxyethyl, 1- or 2-lauroyloxyethyl, 1- or 2-tridecanoyloxyethyl, 1- or 2-myristoyloxyethyl, 1- or 2-pentadecanoyloxyethyl, 1- or 2-palmitoyloxyethyl, 1- or 2-hpetadecanoyloxyethyl, 1- or 2-stearoyloxyethyl, 1or 2-nonadecanoyloxyethyl, 1- or 2-eicosanoyloxyethyl and the like; lower alkoxycarbonyloxy-lower alkyl group, such as methoxycarbonyloxymethyl, ethoxycarbonyloxymethyl, propoxycarbonyloxymethyl, isopropoxycarbonyloxymethyl, tert-butoxycarbonyloxymethyl, 1- or 2-methoxycarbonyloxyethyl, 1- or 2-butoxycarbonyloxyethyl, 1- or 2-isobutoxycarbonyloxyethyl, 1- or 2-tert-butoxycarbonyloxyethyl, 1- or 2-hexyloxycarbonyloxyethyl, 1-, 2- or 3- methoxycarbonyloxypropyl, 1-, 2- or 3-ethoxycarbonyloxypropyl, 1-, 2- or 3-isopropoxycarbonyloxypropyl, 1-, 2-, 3- or 4-ethoxy-carbonyloxybutyl, 1-, 2-, 3- or 4-butoxycarbonyloxybutyl, 1-, 2-, 3-, 4- or 5-pentyloxycarbonyloxypentyl, 1-, 2-, 3-, 4- or 5-neopentyloxycarbonyloxypentyl, 1-, 2-, 3-, 4-, 5- or 6-ethoxycarbonyloxyhexyl and the like; (5-lower alkyl-2-oxo-1,3-dioxol-4-yl)-lower alkyl group, such as (5-methyl-2-oxo-1,3-dioxol-4-yl)-methyl, (5-ethyl-2-oxo-1,3-dioxol-4-yl)-methyl, (5-propyl-2-oxo-1,3-dioxol-4-yl)-ethyl and the like; lower alkanesulfonyl-lower alkyl group, such as mesylmethyl, 2-mesylethyl and the like; ar-lower alkyl group which may contain one substituent or more, such as mono-, di- or tri-phenyl-lower alkyl group which may contain one suitable substituent or more, such as benzyl, 4-methoxybenzyl, 4-nitrobenzyl, phenethyl, benzhydryl, trityl, bis(methoxyphenyl)methyl, 3,4-dimethoxybenzyl, 4-hydroxy-3,5-di-tert-butylbenzyl and the like; aryl group which may contain one suitable substituent or more, such as phenyl, tolyl, tert-butylphenyl, xylyl, 4-nitrophenyl, mesityl, cumenyl, salicyl and the like; aralkyloxy lower alkyl group, such as benzyloxymethyl, benzyloxyethyl and the like; heterocyclic group, such as phthalidyl and the like; so forth.

As the protective group for the carboxyl group there may further be used a silyl group, such as trimethylsilyl, dimethylsilyl, triethylsilyl, t-butyldimethylsilyl, phenyldimethysilyl and the like.

Of the aforesaid protective groups for the carboxyl group, as preferred ones there are cited methyl, ethyl, allyl, tert-butoxycarbonylmethyl, 2-tert-butoxycarbonylethyl, 2,2,2-trichloroethyl, acetoxymethyl, propionyloxymethyl, pivaloyloxymethyl, 1- or 2-acetoxyethyl, 1- or 2-pivaloyloxyethyl, methoxycarbonyloxymethyl, ethoxycarbonyloxymethyl, tert-butoxycarbonyloxymethyl, 1- or 2-ethoxycarbonyloxyethyl, 1- or 2-tertbutoxycarbonyloxyethyl, benzyl, 4-methoxybenzyl, diphenylmethyl, and more preferred are acetoxymethyl, pivaloyloxymethyl, 1- or 2-acetoxyethyl, 1- or 2-ethoxycarbonyloxyethyl, 4-methoxybenzyl, diphenylmethyl and the like.

The "halogen atom" includes 4 halogens of fluorine, chlorine, bromine and iodine atoms, and the "lower alkyl group" may be of either type of straight chain and branched, and there are cited methyl, ethyl, propyl, isopropyl, butyl, isobutyl, sec-butyl, tert-butyl, pentyl, isoamyl, and hexyl groups and the like.

Cephalosporin compounds of said formula (I) the present invention provides contain a 2-protected or unprotected hydroxyimino-2-(2-protected or unprotected aminothiazol-4-yl)-acetamide group in the 7-position of the cephem nucleus, and the protected or unprotected hydroxyimino moiety of this group assumes a geometrical isomerism of either syn-form or anti-form, and thus, compounds of the present invention can exist as of syn-form or anti-form or as a mixture of these both and in general, they should preferably be of syn-form or syn-form based ones.

Further, cephalosporin compounds of the formula (I) by the present invention contains a $R^4$-substituted 1,2,3-thiadiazolylvinyl group in the 3-position of the cephem nucleus, and on the basis of the vinyl group there exist two kinds of geometrical isomerism of (E)-isomer and (Z)-isomer, and compounds of the present invention can assume either form of (E)-isomer, (Z)-isomer and a mixture of these both, and in general, (Z)-isomer is preferred.

In the said 3-substituent, the vinyl group may be bonded to the 1,2,3-thiadiazolyl group either in the 4-position or in the 5-position. Usually it should preferably be bound to the 4-position, and as the substituent $R^4$ on the 1,2,3-thiadiazolyl group a hydrogen atom or methyl group is suitable.

Specific examples of cephalosporin compounds of the formula (I) by the present invention will be shown hereinunder:

7-[(Z)-2-(2-Aminothiazol-4-yl)-2-hydroxyiminoacetamido]-3-[(Z)-2-(1,2,3-thiadiazol-5-yl)vinyl]-3-cephem-4-carboxylic acid, 7-[(Z)-2-(2-aminothiazol-4-yl)-2-hydroxyiminoacetamido]-3-[(E)-2-(1,2,3-thiadiazol-5-yl)vinyl]-3-cephem-4-carboxylic acid, 7-[(Z)-2-(2-aminothiazol-4-yl)-2-hydroxyiminoacetamido]-3-[(Z)-2-(5-methyl-1,2,3-thiadiazol-4-yl)vinyl]-3-cephem-4-carboxylic acid, 7-[(Z)-2-(2-aminothiazol-4-yl)-2-hydroxyiminoacetamido]-3-[(Z)-2-(5-chloro-1,2,3-thiadiazol-4-yl)vinyl]-3-cephem-4-carboxylic acid, 7-[(Z)-2-(2-aminothiazol-4-yl)-2-hydroxyiminoacetamido]-3-[(Z)-2-(4-methyl-1,2,3-thiadiazol-5-yl)vinyl]-3-cephem-4-carboxylic acid, pivaloyloxymethyl 7-[(Z)-2-(2-aminothiazol-4-yl)-2-hydroxyiminoacetamido]-3-[(Z)-2-(1,2,3-thiadiazol-4-yl)vinyl]-3-cephem-4-carboxylate, D,L-1-ethoxycarbonyloxyethyl 7-[(Z)-2-(2-aminothiazol-4-yl)-2-hydroxyiminoacetamido]-3-[(Z)-2-(1,2,3-thiadiazol-4-yl)vinyl]-3-cephem-4-carboxylate, D,L-1-acetoxyethyl 7-[(Z)-2-(2-aminothiazol-4-yl)-2-hydroxyiminoacetamido]-3-[(Z)-2-(1,2,3-thiadiazol-4-yl)vinyl]-3-cephem-4-carboxylate, D,L-1-propionyloxyethyl 7-[(Z)-2-(2-aminothiazol-4-yl)-2-hydroxyiminoacetamido]-3-[(Z)-2-(1,2,3-thiadiazol-4-yl)vinyl]-3-cephem-4-carboxylate, tert-butoxycarbonylmethyl-7-[(Z)-2-(2-aminothiazol-4-yl)-2-hydroxyiminoacetamido]-3-[(Z)-2-(1,2,3-thiadiazol-4-yl)vinyl]-3-cephem-4-carboxylate, (5-methyl-2-oxo-1,3-dioxolen-4-yl)methyl 7-[(Z)-2-(2-aminothiazol-4-yl)-2-hydroxyiminoacetamido]-3-[(Z)-2-(1,2,3-thiadiazol-4-yl)vinyl]-3-cephem-4-carboxylate, phthaliden-3-yl 7-[(Z)-2-(2-aminothiazol-4-yl)-2-hydroxyiminoacetamido]-3-[(Z)-2-(1,2,3-thiadiazol-4-yl)vinyl]-3-cephem-4-carboxylate, acetoxymethyl 7-[(Z)-2-(2-aminothiazol-4-yl)-2-hydroxyiminoacetamido]-3-[(Z)-2-(1,2,3-thiadiazol-4-yl)vinyl]-3-cephem-4-carboxylate, pivaloyloxymethyl 7-[(Z)-2-(2-aminothiazol-4-yl)-2-hydroxyiminoacetamido]-3-[(E)-2-(1,2,3-thiadiazol-4-yl)vinyl]-3-cephem-4-carboxylate, D,L-1-ethoxycarbonyloxyethyl 7-[(Z)-2-(2-aminothiazol-4-yl)-2-hydroxyiminoacetamido]-3-[(E)-2-(1,2,3-thiadiazol-4-yl)vinyl]-3-cephem-4-carboxylate, D,L-1-acetoxyethyl 7-[(Z)-2-(2-aminothiazol-4-yl)-2-hydroxyiminoacetamido]-3-[(E)-2-(1,2,3-thiadiazol-4-yl)vinyl]-3-cephem-4-carboxylate, acetoxymethyl 7-[(Z)-2-(2-aminothiazol-4-yl)-2-hydroxyiminoacetamido]-3-[(E)-2-(1,2,3-thiadiazol-4-yl)vinyl]-3-cephem-4-carboxylate, pivaloyloxymethyl 7-[(Z)-2-(2-aminothiazol-4-yl)-2-hydroxyiminoacetamido]-3-[(E)-2-(1,2,3-thiadiazol-5-yl)vinyl]-3-cephem-4-carboxylate, D,L-1-ethoxycarbonyloxyethyl-7-[(Z)-2-(2-aminothiazol-4-yl)-2-hydroxyiminoacetamido]-3-[(E)-2-(1,2,3-thiadiazol-4-yl)vinyl]-3-cephem-4-carboxylate, D,L-1-acetoxyethyl-7-[(Z)-2-(2-aminothiazol-4-yl)-2-hydroxyiminoacetamido]-3-[(E)-2-(1,2,3-thiadiazol-4-yl)vinyl]-3-cephem-4-carboxylate, acetoxymethyl 7-[(Z)-2-(2-aminothiazol-4-yl)-2-hydroxyiminoacetamido]-3-[(E)-2-(1,2,3-thiadiazol-4-yl)vinyl]-3-cephem-4-carboxylate, pivaloyloxymethyl 7-[(Z)-2-(2-aminothiazol-4-yl)-2-hydroxyiminoacetamido]-3-[(Z)-2-(5-methyl-1,2,3-thiadiazol-4-yl)vinyl]-3-cephem-4-carboxylate, D,L-1-ethoxycarbonyloxyethyl 7-[(Z)-2-(2-aminothiazol-4-yl)-2-hydroxyiminoacetamido]-3-[(Z)-2-(5-methyl-1,2,3-thiadiazol-4-yl)vinyl]-3-cephem-4-carboxylate, D,L-1-acetoxyethyl 7-[(Z)-2-(2-aminothiazol-4-yl)-2-hydroxyiminoacetamido]-3-[(Z)-2-(5-methyl-1,2,3-thiadiazol-4-yl)vinyl]-3-cephem-4-carboxylate, acetoxymethyl 7-[(Z)-2-(2-aminothiazol-4-yl)-2-hydroxyiminoacetamido]-3-[(Z)-2-(5-methyl-1,2,3-thiadiazol-4-yl)vinyl]-3-cephem-4-carboxylate, pivaloyloxymethyl 7-[(Z)-2-(2-aminothiazol-4-yl)-2-hydroxyiminoacetamido]-3-[(Z)-2-(4-methyl-1,2,3-thiadiazol-5-yl)vinyl]-3-cephem-4-carboxylate, D,L-1-ethoxycarbonyloxyethyl 7-[(Z)-2-(2-aminothiazol-4-yl)-2-hydroxyiminoacetamido]-3-[(Z)-2-(4-methyl-1,2,3-thiadiazol-5-yl)vinyl]-3-cephem-4-carboxylate, acetoxymethyl 7-[(Z)-2-(2-aminothiazol-4-yl)-2-hydroxyiminoacetamido]-3-[(Z)-2-(4-methyl-1,2,3-thiadiazol-5-yl)vinyl]-3-cephem-4-carboxylate.

Particularly suitable are the compounds of the formula (I) wherein $R^1$ is a hydrogen atom, $R^2$ is a hydrogen atom, $R^3$ is a hydrogen or methyl, ethyl, allyl, tert-butoxycarbonylmethyl, 2-tert-butoxycarbonylethyl, 2,2,2-trichloroethyl, acetoxymethyl, propionyloxymethyl, pivaloyloxyethyl, 1- or 2-acetoxyethyl, 1- or 2-pivaloyloxyethyl, methoxycarbonyloxymethyl, ethoxycarbonyloxymethyl, tert-butoxycarbonyloxymethyl, 1- or 2-ethoxycarbonyloxyethyl, 1- or 2-tert-butoxycarbonyloxyethyl, benzyl, 4-methoxybenzyl or diphenylmethyl, groups, and $R^4$ is a hydrogen atom or methyl group.

Compounds of the formula (I) may suitably exist as pharmacologically acceptable nontoxic salts, and examples of such salts include salts with inorganic bases, such as alkali metal salts, such as sodium salt, potassium salt and the like, alkaline earth metal salts, such as calcium salt, magnesium salt and the like, and ammonium salt; salts with organic bases, such as triethylamine salt, pyridine salt, picoline salt, dicyclohexylamine salt, N,N-dibenzylethylenediamine salt and the like; salts with inorganic acids, such as hydrochloride, sulfate, phosphate and the like; salts with organic acids, such as acetate, trifluoroacetate, maleate, formate, lactate, tartrate, malate, methanesulfonate, toluenesulfonate and the like; salts with amino acids, such as alginate, asparaginate, glutamate and the like.

The aforesaid compounds of the present invention can be prepared, for example, in the following manner.

(a) A compound represented by the formula

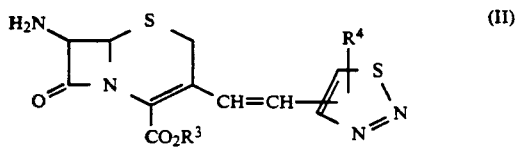

in which $R^3$ and $R^4$ are as defined above, or its derivative being reactive in the amino group or their salts are reacted with a compound represented by the formula

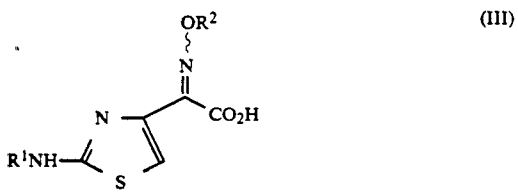

in which $R^1$ is as defined above, or its derivative being reactive in the carboxyl group or their salts, and the amino protective group and/or hydroxyl protective group and/or carboxyl protective group present is optionally split off from the resultant compound of said formula (I) wherein $R^1$ is the protective group for the amino group and/or $R^2$ is the protective group for the hydroxyl group and/or $R^3$ is the protective group for the carboxyl group, and the resultant compound of the formula (I) is optionally converted into its pharmacologically acceptable nontoxic salt, or (b) the compound represented by said formula (II), or its derivative being reactive in the amino group, or their salts are reacted with a compound represented by the formula $$XCH_2COCH_2CO_2H \quad (IV)$$

in which X is a halogen atom, or its derivative being reactive in the carboxyl group, or their salts, the resultant compound represented by the formula

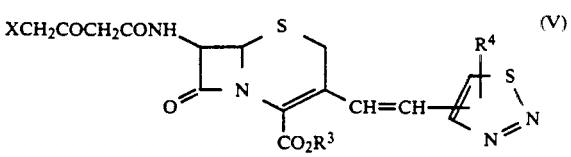

in which $R^3$, $R^4$ and X are as defined above, or its salts are reacted with a nitrosating agent, then the resultant compound represented by the formula

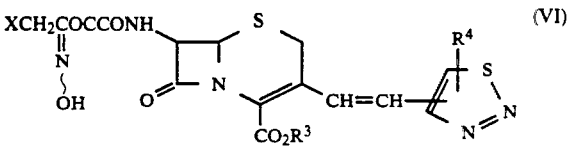

in which $R^3$, $R^4$ and X are as defined above, or its salts are reacted with a thiourea represented by the formula

in which $R^1$ is as defined above, thereby a compound represented by the formula

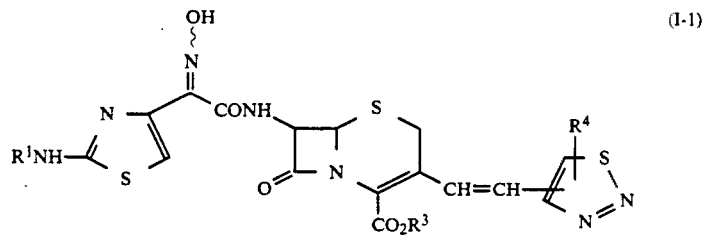

in which $R^1$, $R^3$ and $R^4$ are as defined above, or its salts are prepared and in the case of the compound of the formula (I-1) wherein $R^1$ is a protective group for the amino group and/or $R^3$ is a protective group for the carboxyl group, the amino protective group and/or carboxyl protective group is optionally split off from this compound and the resultant compound of the formula (I-1) is optionally converted into its pharmacologically acceptable nontoxic salt.

In the said process variant (a), as suitable examples of the derivative of the compound (II) being reactive in the amino group there are cited Schiff bases (imine type isomer or enamine type isomer being its tautomer) formed by the reaction of the compound (II) with a carbonyl compound, such as aldehyde, ketone and the like; silyl derivatives obtained by the reaction of the compound (II) with a silyl compound, such as bis(trimethylsilyl)acetamide and the like; or derivatives formed by the reaction of the compound (II) with phosphorus trichloride or phosgene.

As suitable salts of the compound (II) or (III) there are cited an acid addition salt, such as salt with organic acid or inorganic acid, such as acetate, maleate, tartrate, benzenesulfonte, sulfate, phosphate and the like, or metal salt, such as alkali metal salt or alkaline earth metal salt, such as sodium salt, potassium salt, calcium salt, magnesium salt and the like, or ammonium salt or organic amine salt, such as triethylamine salt, dicyclohexylamine salt and the like.

As suitable examples of the derivative of the compound (III) being reactive in the carboxyl group there are cited an acid halide, acid azide, acid anhydride, activated amide, activated ester and the like. More particularly, there are cited an acid chloride and acid bromide; mixed acid anhydride with an acid, such as substituted phosphoric acid (such as diaralkylphosphoric acid, phenylphosphoric acid, diphenylphosphoric acid, dibenzylphosphoric acid, halogenated phosphoric acid and the like, dialkylphosphorous acid, sulphorous acid, thiosulphuric acid, sulphuric acid, alkyl carbonate, such as methyl carbonate, ethyl carbonate and the like, aliphatic carboxylic acid (such as pivalic acid, valeric acid, isovaleric acid, 2-ethylacetic acid, trichloroacetic acid and the like), or aromatic carboxylic acid, such as benzoic acid and the like; symmetrical acid anhydride; activated amide with imidazole, 4-substituted imidazole, dimethylpyrazole, triazole or tetrazole; or activated ester, such as cyanomethyl ester, methoxymethyl ester, dimethyliminomethyl [$(CH_3)_2N=CH-$] ester, vinyl ester, propargyl ester, p-nitrophenyl, 2,4-dinitrophenyl ester, trichlorophenyl ester, pentachlorophenyl ester, mesylphenyl ester, phenylazophenyl ester, phenylthio ester, p-nitrophenylthio ester, p-cresylthio ester, carboxymethylthio ester, pyranyl ester, pyridyl ester, piperidyl ester, 8-quinolylthio ester and the like, or ester with an N-hydroxy compound, such as N,N-dimethylhydroxyamine, 1-hydroxy-2-(1H)-pyridone, N-hydroxysuccinimide, N-hydroxylphthalimide, 1-hydroxy-6-chloro-1H-benztriazole and the like.

These reactive derivatives are optionally chosen according to the kind of the compound (III) used.

The reaction of the compound (II) or its reactive derivative or their salts [which may generally be called the compound (II) hereinunder] with the compound (III) or its reactive derivative or their salts [which may generally be called the compound (III) hereinunder] can be carried out in like manner as the amidation reaction known per se. For instance, the reaction of the compound (II) with the compound (III) is usually carried out in a solvent, such as water, acetone, dioxan, acetonitrile, chloroform, methylene chloride, ethylene chloride, tetrahydrofuran, ethyl acetate, N,N-dimethylformamide, and pyridine, or other optional organic solvents not adversely affecting this reaction. These solvents may be used in admixture with water.

In the case of using the compound (III) as a free acid or salt in this reaction, the reaction should desirably be carried out in the presence of a condensing agent, and as such a condensing agent there are cited, for instance, N,N'-dichlorohexylcarbonyl diimide, N-cyclohexyl-N'-morpholinoethylcarboiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide; N,N'-carbonylbis(2-methylimidazole), pentamethyleneketene-N-cyclohexylimine, diphenylketene-N-cyclohexylimine, ethoxyacetylene; 1-alkoxy-1-chloroethylene, trialkyl phosphite, ethyl polyphosphate, isopropyl polyphosphate; phosphorus oxychloride, phosphorus trichloride, thionyl chloride, oxalyl chloride, triphenyl phosphine, 2-ethyl-7-hydroxybenzisoxazolium salt, 2-ethyl-5-(m-sulfophenyl)isoxazolium hydroxide intramolecular salt, 1-(p-chlorobenzenesulfonyloxy-6-chloro-1H-benzotriazole, so-called Vilsmeyer's reagent obtained by the reaction of dimethylformamide with thionyl chloride, phosgene, phosphorus oxychloride or the like.

These condensing agents may usually be used in a proportion of 1 to 10 mols, preferably 1 to 2 mols, for 1 mol of the compound (III).

This reaction may also be conducted in the presence of an inorganic base or organic base, and as examples of such bases there are cited an alkali metal bicarbonate, such as sodium bicarbonate, potassium bicarbonate and the like, alkali metal carbonate (such as sodium carbonate, potassium carbonate and the like), alkaline earth metal carbonate, such as calcium carbonate and the like, tri-(lower) alkylamine, such as trimethylamine, triethylamine and the like, pyridine, N-(lower) alkylmorpholine, N,N-di-(lower) alkylbenzylamine and the like. The amount of these bases used is not critical, but usually they are suitable used in the range of 1 to 10 mols, preferably 0.5 to 2 mols, for 1 mol of the compound (II).

It is difficult to unconditionally set the temperature for the amidation reaction of the compound (II) with the compound (III) since it is varied over a wide range depending on the kind of these compounds used, whether or not to use the condensing agent and the like but in general, the temperature being in the range of from as low a temperature as $-80°$ C. to the reflux temperature of the reaction mixture, particularly the temperature being in the range of from about $-60°$ C. to about 60° C., is usually well used.

Further, the proportion in which to use the compound (III) for the compound (II) is not strictly restricted, but usually the compound (III) is conveniently used in the range of 1 to 5 mols, preferably 1 to 2 mols, for 1 mol of the compound (II).

The compound of the formula (I) by the present invention is obtained by the said amidation reaction, but in the compound of the formula (I) wherein $R^3$ is the carboxyl group, the compound can be converted into the corresponding compound of the formula (I) wherein $R^3$ is the hydrogen atom by subjecting to the splitting-off reaction of the carboxyl protective group. The splitting-off reaction of the carboxy protective group can be conducted by the procedure of hydrolysis, hydrogenolysis or the like being usually employed in the splitting-off of the carboxyl protective group. In the case, for instance, where the carboxyl protective group is a silyl group, tert-butoxy group, p-methoxybenzyl group or benzhydryl group, it can be readily be split off by the usual acid hydrolysis.

In the case, further, of the compound (I) wherein $R^1$ is the protective group for the amino group, the compound of the formula (I) can be converted to the corresponding compound of the formula (I) wherein $R^1$ is the hydrogen atom by subjecting to the amino protective group-splitting-off reaction. This amino protective group-splitting-off reaction can be conducted by the heretofore-known procedure, such as hydrolysis, hydrogenolysis and the like. In the case, for instance, where the amino protective group is a formyl group, trityl group, tert-butoxycarbonyl group, benzyloxycarbonyl group or the like, these protective groups can be split off by the conventional acid hydrolysis.

In the case, further, of the compound of the formula (I) wherein $R^2$ is the protective group for the hydroxyl group, the compound of the formula (I) may optionally be subjected to the splitting-off reaction of the protective group for the hydroxyl group thereby there can be prepared the corresponding compound of the formula (I) wherein $R^2$ is the hydrogen atom. The splitting-off reaction of the hydroxyl group can be carried out by employing procedures known per se in the chemical fields of penicillin and cephalosporin, for instance, such means as hydrolysis, hydrogenolysis and the like. In the case, for instance, where the protective group for the hydroxyl group is a silyl group, trityl group, tetrahydropyranyl group, acetyl group and the like, these protective groups can be split off by the usual acid hydrolysis.

In the compound of the formula (I) wherein either two of $R^1$, $R^2$ and $R^3$ are the protective group or three of them are all the protective group, the splitting-off of a plurality of these protective groups may simultaneously be carried out or may be carried out stepwise in sequence.

The compound of the formula (I) obtained can be separated and/or purified from the reaction mixture by procedures known per se, such as crystallization, chromatography, extraction, and the like.

What is more, the compound of the formula (I) obtained may optionally be converted into its pharmacologically acceptable nontoxic salt using the salt-forming reaction known per se.

In the said process variant (b), first, as a first stage, the compound (I-1) or its salt is prepared by the reaction of the compound (II) or its derivative being reactive in the amino group or its salt with the compound (IV) or its derivative being reactive in the carboxyl group or its salt [which may generally be called the compound (IV) hereinunder].

As the derivative of the compound (II) being reactive in the amino group it can be chosen from those which were mentioned in the process variant (a). For instance, there can be cited silyl derivatives formed by the reaction of the compound (II) with a silyl compound, such as trimethylsilylacetamide, bis(trimethylsilyl)acetamide, bis(trimethylsilyl)-urea and the like, and as the reactive derivative of the compound (IV) there is cited an acid halide, such as acid chloride and acid bromide, and these acid halides can be prepared, for instance, by the reaction of a diketone and a halogen.

The reaction of the compound (II) and the compound (IV) is usually carried out in optional solvents not adversely affecting the reaction, such as water, acetone, dioxan, acetonitrile, chloroform, benzene, methylene chloride, ethylene chloride, tetrahydrofuran, ethyl acetate, N,N-dimethylformamide, pyridine, hexamethylformamide and the like, or their mixtures.

The amidation reaction between the compound (II) and the compound (IV) can be carried out at the same reaction conditions as mentioned for the amidation reaction between the compound (II) and the compound (III) in the process variant (a).

The compound (V) obtained by the amidation reaction or its salt is then reacted with a nitrosating agent thereby it can be converted into the compound of the formula (VI) or its salt. As the nitrosating agent used here there can be cited a nitrosyl halide, such as nitrosyl chloride, nitrosyl bromide and the like; alkali metal phosphite, such as sodium phosphite, potassium phosphite and the like; alkyl phosphite, such as butyl phosphite, pentyl phosphite, isoamyl phosphite and the like, and so forth. These nitrosating agents may be used in the range of usually 1 to 10 mols, preferably 1 to 5 mols, for 1 mol of the compound (V).

In the case of using, as the nitrosating agent, a salt of nitrous acid, such as its alkali metal salt, the reaction should preferably be conducted in the presence of an inorganic or organic acid, such as hydrochloric acid, sulfuric acid, formic acid, acetic acid and the like. The amount of the acid used should suitably fall in the range of 1 to 100 mols, preferably 1 to 10 mols, for 1 mol of the compound (V).

This reaction should preferably be carried out in the presence of an activated methylene compound, such as acetylacetone, ethyl acetoacetate and the like. In general, the amount of it used should suitably fall in the range of 1 to 10 mols, preferably 1 to 5 mols, for 1 mol of the compound (V).

This reaction is usually carried out in conventional solvents not adversely affecting the reaction, such as water, acetic acid, benzene, methanol, ethanol, tetrahydrofuran, methylene chloride and the like, or their mixtures.

The reaction temperature may be varied according to the kind of the nitrosating agent used or the like, but it may be set as falling in the range of usually about $-80°$ C. to nearly room temperature, preferably about $-30°$ to about $20°$ C.

Thus, the compound (VI) is formed and this one is reacted with the thiourea (VII). This reaction can usually be carried out in conventional solvents not adversely affecting the reaction, such as ethyl acetate, dichloromethane, chloroform, tetrahydrofuran, N,N'-dimethylformamide, N,N'-dimethylacetoamide, dioxan, water, acetic acid, formic acid and the like, or their mixtures at a temperature falling in the range of from about $20°$ C. to the reflux temperature of the reaction mixture, preferably from about $20°$ to $60°$ C.

The thiourea (VI) should conveniently be used in the range of usually 1 to 10 mols, preferably 1 to 3 mols, for 1 mol of the compound (VI).

By following the said procedure there can be prepared the compound of the formula (I) wherein $R^3$ is the hydrogen atom, viz., the compound of the formula (I-1). In the case of the compound of the formula (I-1) wherein $R^1$ is the protective group for the amino group and/or $R^3$ is the protective group for the carboxyl group, these amino protective group and/or carboxyl protective group can be split off in like manner as mentioned for the process variant (a).

Furthermore, the separation and purification of the compound of the formula (I-1) obtained and conversion of its pharmacologically acceptable nontoxic salt from the compound of the formula (I-1) can also be conducted in like manner as mentioned above.

The compound of the formula (II) used as the starting material in the said processes is a novel compound which has never been disclosed in literature, and it can be prepared, for instance, in such a manner as shown by the following reaction formula.

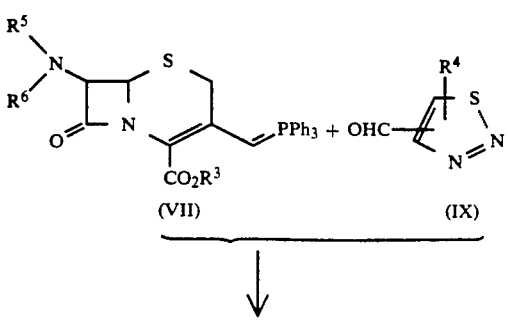

-continued

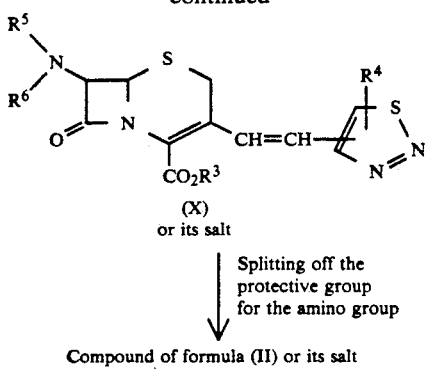

(X) or its salt

↓ Splitting off the protective group for the amino group

Compound of formula (II) or its salt in which
one of $R^5$ and $R^6$ is a hydrogen atom and the other is the same protective group for the amino group as mentioned above for $R^1$, or $R^5$ and $R^6$ may together form an amino protective group, such as phthaloyl group, dimethylaminomethylene group, benzylidene group, substituted benzylidene group, such as N-salicylideneamine and the like,
Ph is a phenyl group,
$R^3$ and $R^4$ are as defined above.

The phosphorus-ylide of the formula (VIII) used as the starting material in the same reaction can be prepared by following the procedure disclosed in J. Antibiotics, 38, 1738 (1985), for instance. Further, the aldehyde of the formula (IX) can be synthesized by following the procedure disclosed in J. Heterocycle, Chem., 7, 415 (1970), for instance.

The reaction of the phosphorous-ylide (VIII) and the aldehyde (IX) may usually be carried out in tetrahydrofuran, dioxan, methylene chloride, dimethylformamide, water or their mixed solvents at a temperature being in the range of about −80° to about 80° C., preferably in the vicinity of room temperature. A proportion of the aldehyde (IX) used for the phosphorus-ylide (VIII) is not particularly restricted, but in general, the aldehyde (IX) can be used in the range of 1 to 5 mols, preferably 1 to 2 mols, for 1 mol of the phosphorus-ylide (VIII).

The compound (X) obtained by the said reaction or its salt is then subjected to the splitting-off reaction of the protective group for the amino group thereby the compound of the formula (II) or its salt can be prepared. The splitting-off reaction of the amino protective group can be carried out in like manner as usually employed, such as hydrolysis, hydrogenolysis, reaction with the Lewis' acid and the like. In the case, for instance, where the amino protective group is an alkoxycarbonyl group, formyl group, trityl group and the like, it can be split off by hydrolysis with an organic or inorganic acid, such as formic acid, trifluoroacetic acid, p-toluenesulfonic acid, hydrochloric acid, sulfuric acid and the like. The acid hydrolysis may be carried out in the presence of nonsolvent or it may be conducted in water, a hydrophilic organic solvent or water-organic mixed solvent. In the case of using trifluoroacetic acid the reaction can also be conducted in the presence of anisole.

Moreover, the splitting-off of the amino protective group can be effected by reacting the compound (X) with an iminohalogenation agent and successively with an iminoetherification agent and optionally subjecting the compound produced by hydrolysis.

The compound of the formula (X) or (II) wherein $R^3$ is the protective group for the carboxyl group may optionally be subjected to the said splitting-off reaction of the carboxyl protective group thereby it can be converted into the corresponding compound of the formula (X) or (II) wherein $R^3$ is the hydrogen atom.

The compound of the formula (II) obtained or its salt can be separated from the reaction mixture and/or purified by following the procedure known per se, such as crystallization, chromatography and extraction.

Cephalosporin compounds of the formula (I) the present invention provides exhibit their strong anti-bacterial activity against a wide range of gram-positive and gram-negative bacteria, and are valuable as medicaments used in prevention or treatment of bacterial infectious diseases.

The anti-bacterial activity of the compounds of the present invention can be proved by their in-vitro and in-vivo tests.

(1) In-vitro anitbacterial activity test

Compounds prepared in the hereinbelow-described Examples were tested for their minimum growth inhibitory concentration (MIC) (unit: µg/ml) by following the procedure set forth by the Committee on Revision of Minimum Growth Inhibitory Concentration Measurement Methods of Japan Chemotherapy Society (refer to Chemotherapy, Vol. 29, No. 1, pp.76–79 (1981)]. The result was shown in following Table 1.

TABLE 1

| Bacteria tested | Minimum growth inhibitory concentration (µg/ml) | | | | |
|---|---|---|---|---|---|
| | Example No. | | | | |
| | 5 | 14 | 18 | 21 | A |
| S. aureus 209 P-JC | ≦0.025 | 0.1 | 0.2 | 0.2 | 12.5 |
| P. mirabilis IFO 3849 | 0.1 | 0.39 | 0.39 | 0.39 | ≦0.025 |

Note: In the table the standard product is CFIS {7-[(Z)-2-(2-amino-4-thiazolyl)-2-(carboxymethyloximino)acetamido]-3-vinyl-3-cephem-4-carboxylic acid (2) In-vivo absorption test A Wistar type rat (male) was fasted overnight, then 50 mg/kg of an active compound was once orally administered, blood was taken after the lapse of a time indicated in following table and the blood concentration of the active compound was measured by bioassay using, as the strain being tested, Bacirus cereus S1101 strain [refer to Chemotherapy, Vol. 22, No. 6, 1124–1129]. The result was shown in following Table 2.

TABLE 2

| Example No. | Blood concentration Serum concentration (µg/ml) Time after oral administration (hr) | | |
|---|---|---|---|
| | 1 | 2 | 4 |
| 5 | 4.8 | 6.0 | 6.0 |
| 19 | 11.3 | 9.8 | 5.8 |
| 22 | 26.6 | 37.8 | 26.7 |
| 23 | 72.1 | 56.6 | 33.4 |

The compound of the formula (I) by the present invention or its pharmacologically acceptable nontoxic salt can be administered, as an antibacterial agent, to humans or animals other than humans orally, parenterally, perrectally, permucosally or locally. In its administration the compound of the present invention can be formulated in a dosage form suitable for administration according to the usual galenical preparation method—in such various dosage forms as solid preparation, such as tablet, granule, powder, capsulem, freeze-dried powder, pill, troche, sublingual agent and the like; liquid preparation, such as aqueous or oily suspension, solution, emulsion, syrup, elixir, spray agent and the like; local preparation; such as suppository, ointment, cream, lotion, powder and the like; pharyngo-paint; and so forth.

As adjuvants used in those preparations there can be cited a binder, such as syrup, gum arabi, gelatin, sorbitol, tragacanth, polyvinyl pyrrolidone and the like; filler, such as lactose, sugar, corn, starch, calcium phosphate, sorbitol, glycine and the like; lubricant, such as magnesium stearate, talc, polyethylene glycol, silica and the like; disintegrator, such as potato starch, sodium carbonate, calcium carbonate and the like; wetting agent, such as sodium lauryl sulfate, calcium stearate, magnesium stearate and the like; solvent, such as water, ethyl alcohol, ethyl acetate, benzyl alcohol and the like; suspension, such as sorbitol syrup, methyl cellulose, glucose/sugar syrup, gelatin, hydroxyethyl cellulose, carboxymethyl cellulose, hydrogenated edible fat and the like; emulsifier, such as lecithine, sorbitan monooleate, gum arabi, glycerin, polyethylene glycol and the like; antiseptic, such as methyl p-hydroxybenzoate; cocoa cream, paraffin, glycerine, vaseline and so forth.

The preparation containing the compound of the present invention may be in a unit dosage form, and the content of the active compound is varied according to the form of the preparation or route of administration, but in general, it may be contained in the range of at least 0.1 weight %, preferably 0.5 to 95 weight %.

Further, the dose of the compound of the present invention is varied according to the degree of seriousness or lightness of the disease being the subject of administration, male, age, body weight or the like and administration route or the like, but it can be mentioned as a standard in a way that in the case of adult it is administered in the range of 0.5 to 500 mg/kg, preferably 5 to 100 mg/kg, per day. It may, of course, deviate from this range according to the judgment of doctor or the like. The said dose may optionally be administered in portions.

The present invention will be explained by way of Examples in more detail hereinunder.

REFERENTIAL EXAMPLE 1

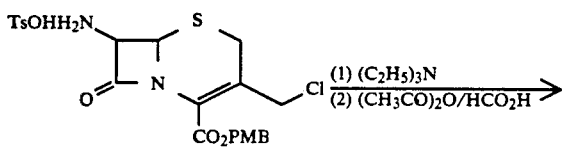

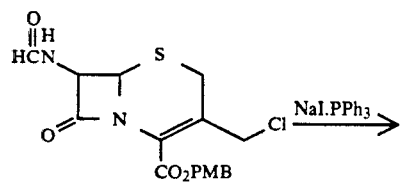

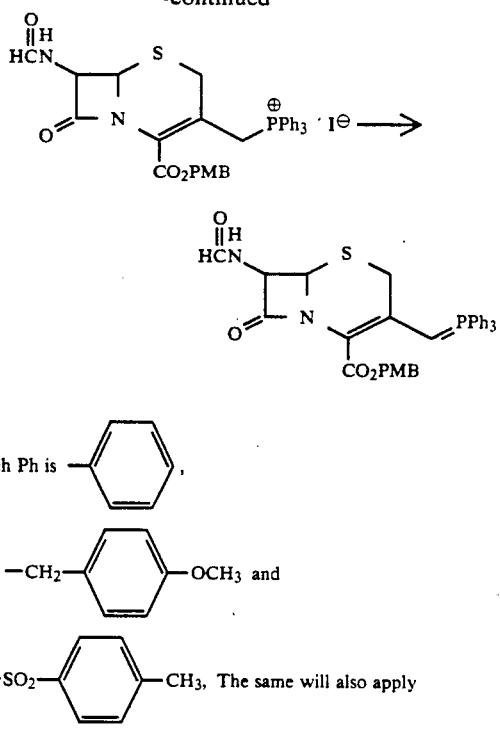

(in which Ph is —⌬,

PMB is —CH$_2$—⌬—OCH$_3$ and

Ts is —SO$_2$—⌬—CH$_3$, The same will also apply hereinafter.)

Formic acid (4.3 g, 0.093 mol) and acetic anhydride (9.4 g, 0.093 mol) were mixed and stirred at 50° C. for 1 hour. p-Toluenesulfonate of p-methoxybenzyl 7-amino-3-chloromethyl-3-cephem-4-carboxylate (10 g, 0.019 mol) was suspended in dried THF (30 ml) and dissolved by adding triethylamine (1.87 g, 0.019 mol) in portions. After cooling with ice the formic acid-acetic anhydride mixed solution was cooled down to room temperature, and the residue was dissolved by addition of ethyl acetate (250 ml) and a small amount of saturated sodium bicarbonate. The organic layer was separated. The aqueous layer was further extracted with ethyl acetate. The organic layer put together was dried, filtered and concentrated, and the residue was cleansed with hexane and as crystal p-methoxybenzyl 3-chloromethyl-7-formylamino-3-cephem-4-carboxylate (7 g) was obtained.

$^1$H-NMR (DMSO$_4$-d$_6$) δ: 3.67 (q$_{AB}$, J=18Hz, 2H), 3.78 (s, 3H), 4.55 (bs, 2H), 5.22 (d, J=2Hz, 1H), 5.27 (s, 2H), 5.87 (dd, J=4Hz, J=8Hz, 1H), 6.97 (d, J=9Hz, 2H), 8.16 (s, 1H), 9.10 (d, J=8Hz, 1H).

The said 3-chloromethyl compound (78 g, 0.018 mol) was dissolved in DMF (20 ml). By addition of sodium iodide (2.7 g, 0.018 mol) and triphenyl phosphine (7.1 g, 0.027 mol) it was dissolved and stirred at room temperature for 2 days. It was poured into a mixed solution of isopropyl ether (400 ml) and isopropyl alcohol (400 ml). Precipitates were filtered off thereby there was obtained [7-formylamino-4-(4-methoxybenzyloxycarbonyl)-3-cephem-3-ylmethyl]-triphenylphosphonium iodide (6.6 g).

$^1$H-NMR (DMSO-d$_6$) δ: 3.64 (q$_{AB}$, J=18Hz, 2H), 3.80 (s, 3H), 4.76 (q$_{AB}$, J=16Hz, 2H), 5.14 (s, 2H), 5.33 (dd, J=4Hz, J=8Hz, 1H), 6.94 (d, J=9Hz, 2H), 7.24 (d, J=10Hz, 2H), 7.87 (s, 5H), 8.18 (s, 1H). 9.17 (d, J=8Hz, 1H).

The said phosphonium salt (0.5 g, 0.67 mol) was dissolved in methylene chloride (5 ml). By addition of 1N sodium hydroxide solution (0.75 ml) it was stirred at room temperature for 15 minutes. The organic layer was cleansed with aqueous sodium chloride solution until the aqueous layer turned natural. After that, it was dried and concentrated, and residual precipitates were cleansed with hexane thereby p-methoxybenzyl 7-formylamino-3-triphenylphosphoranilidenemethyl-3-cephem-4-carboxylate (0.32 g) was obtained.

$^1$H-NMR (DMSO-d$_6$) δ: 3.2-3.6 (m, 2H), 3.77 (s, 3H), 5.07 (s, 2H), 5.13 (d, J=4Hz, 1H), 5.23 (dd, J=4Hz, J=8Hz, 1H), 5.48 (d, J=22.5Hz, 1H), 6.92 (d, J=10Hz, 2H), 7.53 (d, J=10Hz, 2H), 7.77 (s. 5H), 8.13 (s, 1H), 8.81 (d, J=8Hz, 1H).

IR (KBr): 3250, 3050, 2950, 1760, 1680, 1620, 1510, 1480, 1440, 1390, 1300, 1240, 1220, 1170, 1100, 1036, 1010, 1000, 890, 820, 750, 720, 690, 520, 500 cm$^{-1}$.

EXAMPLE 1

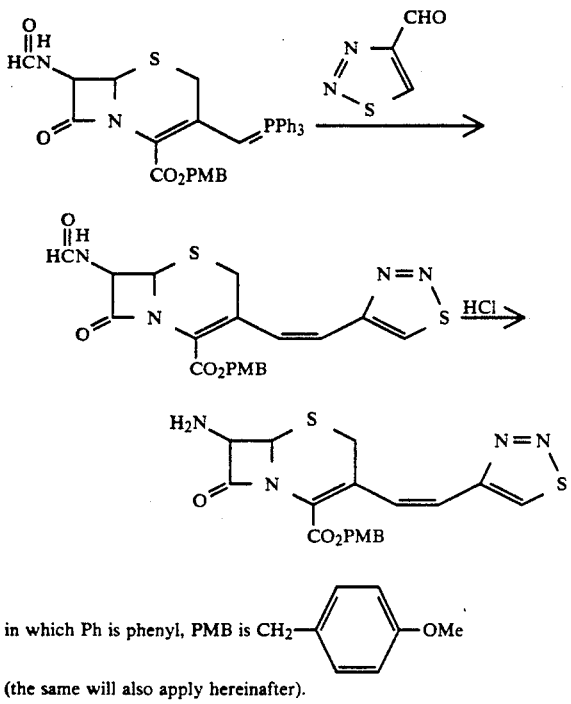

in which Ph is phenyl, PMB is CH$_2$—⟨C$_6$H$_4$⟩—OMe (the same will also apply hereinafter).

p-Methoxybenzyl 7-formylamino-3-triphenylphosphoranilidenemethyl-3-cephem-4-carboxylate (3 g) was dissolved in methylene chloride (20 ml) and 4-formyl-1,2,3-thiadiazole (1 g, 8.8 mmol) was added. It was stirred at room temperature overnight and the solvent was distilled off under reduced pressure and then it was purified by silica gel column chromatography thereby p-methoxybenzyl 7-formylamino-3-[(Z)-2-(1,2,3-thiadiazol-4-yl)vinyl]-3-cephem-4-carboxylate (0.6 g) was obtained as a yellow powder.

$^1$H-NMR (DMSO-d$_6$): 3.68 (q$_{AB}$, J=18Hz, 2H), 3.78 (s, 3H), 5.03 (s, 2H), 5.27 (d, J=5Hz, 1H), 5.86 (dd, J=9Hz, J=5Hz, 1H), 6.72 (d, J=12Hz, 1H), 6.92 (d, J=9Hz, 2H), 6.97 (d, J=12Hz, 1H), 7.28 (d, J=9Hz, 2H), 8.18 (s, 1H), 9.04 (s, 1H), 9.13 (d, J=9Hz, 1H).

The said ester (0.6 g, 1.3 mmol) was dissolved in methanol (10 ml). By addition of concentrated hydrochloric acid (0.1 ml) it was stirred at room temperature for 2 hours. After the solvent was distilled off, a small amount of water was added to the residue and aqueous saturated sodium bicarbonate solution was added to adjust to pH 8-9. It was dissolved by addition of ethyl acetate and the oganic layer was separated. The organic layer was dried and the solvent was dissolved off, and the residue was purified by silica gel column chromatography thereby p-methoxybenzyl 7-amino-3-[(Z)-2-(1,2,3-thiadiazol-4-yl)vinyl]-3-cephem-4-carboxylate (0.21 g) was obtained as a yellow powder solid.

$^1$H-NMR (DMSO-d$_6$) δ: 3.56 (q$_{AB}$, J=18Hz, 2H), 3.77 (s, 3H), 5.03 (s, 2H), 5.16 (d, J=5Hz, 1H), 6.68 (d, J=12Hz, 1H), 6.93 (d, J=9Hz, 2H), 6.96 (d, J=12Hz, 1H), 7.28 (d, J=9Hz, 2H), 9.03 (s, 1H).

EXAMPLE 2

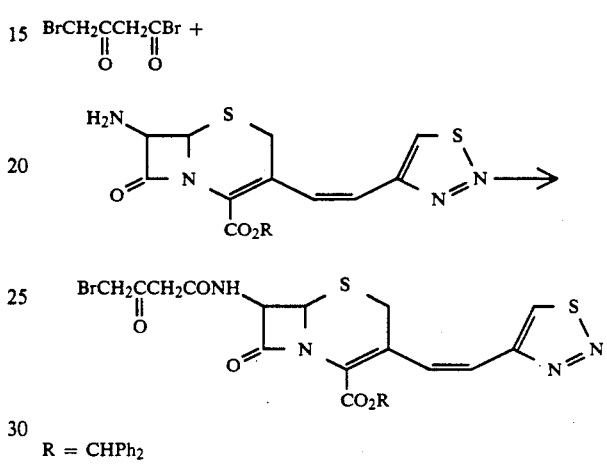

R = CHPh$_2$

Diphenylmethyl 7-amino-3-[(Z)-2-(1,2,3-thiadiazol-4-yl)vinyl]-3-cephem-4-carboxylate (5.20 g, 11 mol) was suspended in a mixed solvent of THF-methylene chloride (1:1, 100 ml) and by addition of bistrimethylsilylacetamide (5.84 g, 28 mmol) it was stirred at room temperature. Added under cooling at −20° C. to this solution was 4-bromoacetoacetyl bromide obtained from diketene (1.11 g, 13 mmols) and bromien (0.67 ml, 13 mmols) in methylene chloride (5 ml), and the reaction mixture was stirred at −10° C. for 1 hour. Ethyl acetate (100 ml) and water (30 ml) were added to the reaction solution. The organic layer was separated, washed with water and saline solution and then dried over magnesium sulfate. The solvent was distilled off, then diisopropyl ether (100 ml) was added to the residue and it was stirred at 0° C. for 1 hour thereby diphenylmethyl 7-(4-bromoacetoacetamido)-3[(Z)-2-(1,2,3-thiadiazol-4-yl)vinyl]-3-cephem-4-carboxylate (7.0 g) was obtained as a yellow powder compound.

$^1$H-NMR (CDCl$_3$) δ: 3.33 (q$_{AB}$, J=18Hz, 2H), 3.72-3.90 (m, 4H), 5.00 (d, J=4.5Hz, 1H), 5.76 (dd, J=4.5Hz, J=9Hz, 1H), 6.63 (s, 1H), 6.70 (d, J=12Hz, 1H), 7.16 (m, 11H), 8.10 (s, 1H).

IR (KBr): 3050, 2950, 1780, 1730, 1590, 1520, 1400, 1320, 1215, 1120, 1000, 890, 730, 700 cm$^{-1}$.

EXAMPLE 3

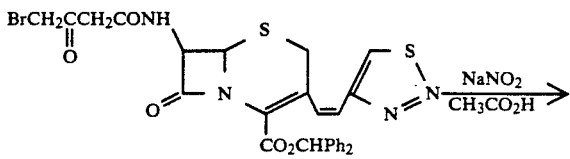

-continued

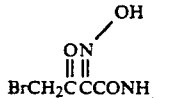

J=9Hz, 1H), 6.69 (s, 1H), 6.76 (d, J=12Hz, 1H), 7.23 (m, 11H), 8.17 (s, 1H), 9.33 (d, J=9Hz, 1H).

IR (KBr): 3300, 3050, 1790, 1730, 1600, 1550, 1380, 1225, 1180, 1010, 760, 700 cm$^{-1}$.

EXAMPLE 4

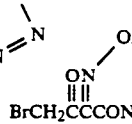
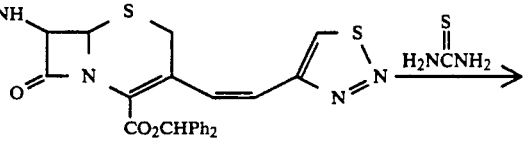

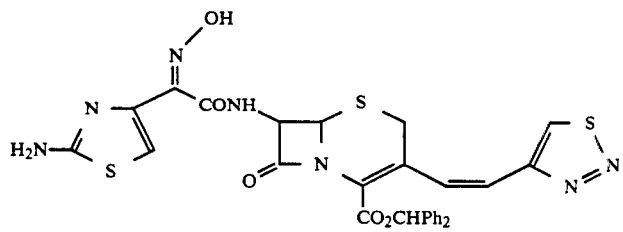

A methylene chloride-acetic acid (20 ml–10 ml) solution of diphenylmethyl 7-(4-bromoacetoacetamido)-3-[(Z)-2-(1,2,3-thiadiazol-4-yl)vinyl]-3-cephem-4-carboxylate (2.22 g, 3.4 mmol) was cooled from −7° C. to −5° C. and an aqueous solution (2 ml) of sodium nitrite (0.32 g, 4.6 mmol) was added in portions. After its dropwise addition the mixture was stirred for 30 minutes, then urea (0.3 g) was added and the temperature of the reaction solution was returned to room temperature. The reaction mixture was extracted with methylene chloride, then washed with water (40 ml×2) and then dried over magnesium sulfate. When the solvent was distilled off, diphenylmethyl 7-(4-bromo-2-hydroxyiminoacetoacetamido)-3-[(Z)-2-(1,2,3-thiadiazol-4-yl)vinyl]-3-cephem-4-carboxylate (1.85 g) was obtained as a light yellow powder compound.

$^1$H-NMR (CDCl$_3$) δ: 3.50 (q$_{AB}$, J=18Hz, 2H), 4.46 (s, 2H), 5.13 (d, J=4.5Hz, 1H), 5.83 (dd, J=4.5Hz,

Diphenyl 7-(4-bromo-2-hydroxyiminoacetoacetamido)-3-[(Z)-2-(1,2,3-thiadiazol-4-yl)vinyl]-3-cephem-4-carboxylate (1.85 g, 2.7 mmol) was dissolved in N,N′-dimethylacetamide (6 ml) and thiourea (0.23 g, 3 mmol) was added. The reaction solution was stirred at room temperature for 1 hour and then, the reaction solution was added in portions in 3% aqueous sodium bicarbonate solution (65 ml). It was extracted with ethyl acetate and cleansed with saline solution, and the extract was dried over magnesium sulfate. After the solvent was distilled off, the residue was pulverized in isopropyl ether and collected by filtration, cleansed with diisopropyl ether and dried thereby diphenylmethyl 7-[(Z)-2-(2-aminothiazol-4-yl)-2-hydroxyiminoacetamido]-3-[(Z)-2-(1,2,3-thiadiazol-4-yl)vinyl]-3-cephem-4-carboxylate (1.6 g) was obtained.

$^1$H-NMR (CDCl$_3$): 3.43 (m, 2H), 5.07 (d, J=4.5Hz, 1H), 5.89 (dd, J=4.5Hz, J=9Hz, 1H), 6.76 (d, J=12Hz, 1H), 6.89 (s, 1H), 7.23 (m, 13H), 8.21 (s, 1H), 9.66 (d, J=9Hz), 1H).

IR (KBr): 3350, 3120, 1785, 1730, 1620, 1530, 1375, 1300, 1225, 1180, 1100, 1010, 800, 760, 700 cm$^{-1}$.

EXAMPLE 5

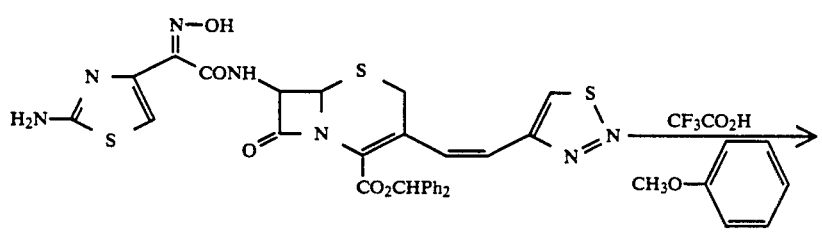

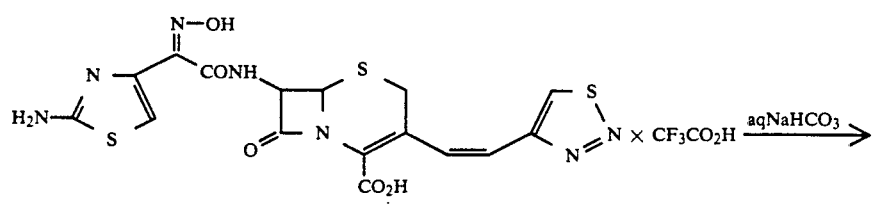

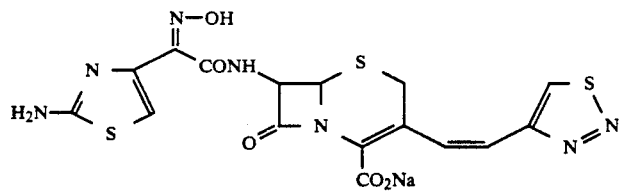

Diphenylmethyl-7-[(Z)-2-(2-aminothiazol-4-yl)-2-hydroxyiminoacetamido]-3-[(Z)-2-(1,2,3-thiadiazol-4-yl)vinyl]-3-cephem-4-carboxylate (1.6 g, 2.6 mmol) was added to a mixed solution of trifluoroacetic acid-anisole (3 ml—3 m l) cooled to 0° C. The reaction solution was stirred at 5° C. for 1.5 hours. The reaction solution was added in diisopropyl ether (100 ml) and stirred. Precipitates were collected by filtration, cleansed with diisopropyl ether and dried thereby trifluoroacetate of 7-[(Z)-2-(2-aminothiazol-4-yl)-2-hydroxyiminoacetamido]-3-[(Z)-2-(1,2,3-thiadiazol-4-yl)vinyl]-3-cephem-4-carboxylic acid (1.13 g) was obtained.

$^1$H-NMR (DMSO-d$_6$) δ: 3.50 (m, 2H), 5.20 (d, J=4.5Hz, 1H), 5.76 (dd, J=4.5Hz, J=9Hz, 1H), 6.66 (d, J=12Hz, 1H), 6.83 (s, 1H), 6.92 (d, J=12Hz, 1H), 7.33 (bs, 2H), 9.00 (s, 1H), 9.50 (d, J=9Hz, 1H).

IR (KBr): 3300, 3100, 1780, 1680, 1600, 1540, 1410, 1360, 1240, 1200, 1140, 1010, 800, 720 cm$^{-1}$.

The trifluoroacetate obtained in the said reaction (4.37 g) was dissolved in aqueous sodium bicarbonate solution and purified by HP-20 column chromatography thereby sodium 7-[(Z)-2-(2-aminothiazol-4-yl)-2-hydroxyiminoacetamido]-3-[(Z)-2-(1,2,3-thiadiazol-4-yl)vinyl]-3-cephem-4-carboxylate (0.94 g) was obtained.

$^1$H-NMR (D$_2$O) δ: 3.17 , 3.52 (q$_{AB}$, J=18Hz, 2H), 5.21 (d, J=5Hz, 1H), 5.73 (d, J=5Hz, 1H), 6.54 (d, J=12Hz, 1H), 6.80 (d, J=12Hz, 1H), 6.87 (s, 1H), 8.68 (s, 1H).

IR (KBr): 3350, 1760, 1670, 1610, 1530, 1390, 1350, 1185, 1090, 1055, 980 cm$^{-1}$.

(Z)-2-(2-tritylaminothiazol-4-yl)-2-trityloxyiminoacetic acid (2.09 g, 3.10 mmol) was dissolved in methylene chloride (40 ml) and cooled with ice. By addition of DCC (0.95 g, 4.65 mmol) it was stirred for 30 minutes. Added to this reaction solution was p-methoxybenzyl 7-amino-3-[(Z)-2-(1,2,3-thiadiazol-4-yl)vinyl]-3-cephem-4-carboxylate (1.30 g, 3.0 mmol), and it was stirred at room temperature for 16 hours. After the reaction the reaction solution was filtered and then the filtrate was concentrated under reduced pressure. The residue was purified by column chromatography thereby p-methoxybenzyl 7-[(Z)-2-(2-tritylaminothiazol-4-yl)-2-trityloxyiminioacetamido]-3-[(Z)-2-(1,2,3-thiadiazol-4-yl)vinyl]-3-cephem-4-carboxylate (0.28 g, 9% yield) was obtained as a yellow powdered compound.

$^1$H-NMR (CDCl$_3$) δ: 3.23 (q$_{AB}$, J=16Hz, 2H), 3.63 (s, 3H), 4.92 (d, J=4.5Hz, 1H), 4.89 (s, 2H), 6.03 (dd, J=4.5Hz, J=9Hz, 1H), 6.40 (s, 1H), 6.73–7.00 (m, 2H), 7.07–7.43 (m, 30H), 8.16 (s, 1H), 8.16 (d, J=9Hz, 1H).

IR (KBr): 3300, 2930, 1780, 1720, 1680, 1510, 1440, 1360, 1300, 1240, 1170, 1030, 960, 820, 750, 700, 630 m$^{-1}$.

The compound (0.25 g) obtained in the said reaction was dissolved in THF (10 ml) and it was stirred at 50° C. for 20 minutes by addition of 50% aqueous formic acid (3 ml). The reaction solution was concentrated under reduced pressure, then trifluoroacetic acid (5 ml) was added to the residue and it was stirred at room temperature for 20 minutes. The reaction solution was concen-

EXAMPLE 6

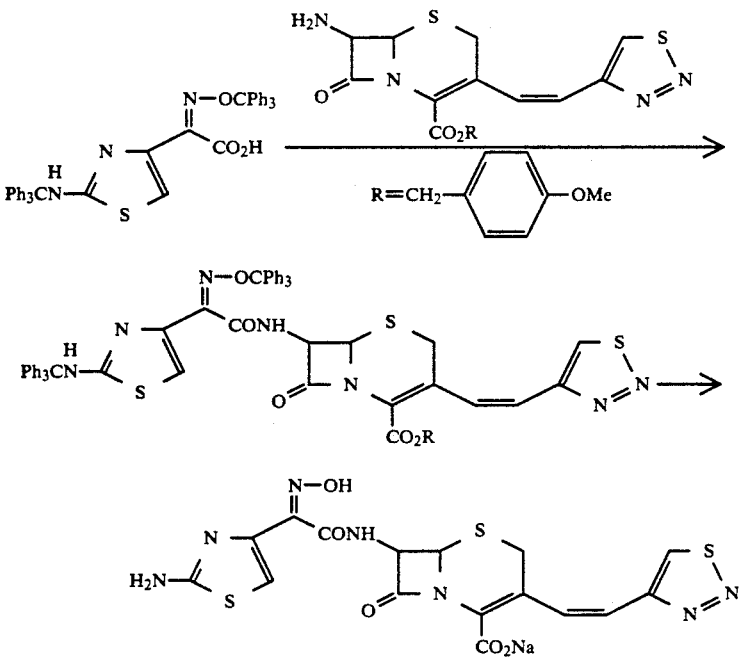

EXAMPLE 7

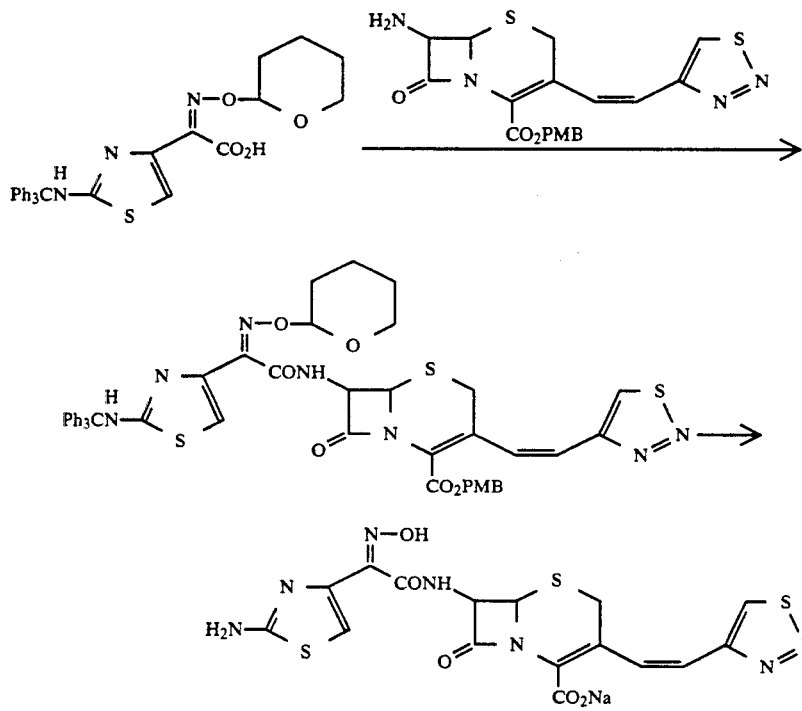

(Z)-2-(2-tritylaminothiazol-4-yl)-2-tetrahydropyranyloxyiminoacetic acid (0.39 g, 0.76 mmol) and p-methoxybenzyl 7-amino-3-[(Z)-2-(1,2,3-thiadiazol-4-yl)vinyl]-3-cephem-4-carboxylate (1.33 g, 0.76 mmol) were dissolved in methylene chloride (10 ml) and stirred at room temperature for 12 hours by addition of DCC (0.18 g, 0.87 mmol). Insolubles were filtered and then the filtrate was concentrated under reduced pressure. The residue was purified by column chromatography thereby p-methoxybenzyl 7-[(Z)-2-(2-tritylaminothiazol-4-yl)-2-tetrahydropyranyloxyiminoacetamido]-3-[(Z)-2-(1,2,3-thiadiazol-4-yl)vinyl]-3-cephem-4-carboxylate (0.25 g) was obtained as a light yellow powder compound.

$^1$H-NMR (CDCl$_3$) δ: 1.4–1.9 (m, 6H), 3.43 (q$_{AB}$, J=18Hz, 2H), 3.43 (m, 2H), 5.13 (d, J=4.5Hz, 1H), 5.10 (s, 2H), 5.50 (m, 1H), 6.00 (dd, J=4.5Hz, J=9Hz, 1H), 6.70–7.00 (m, 5H), 7.20–7.40 (m, 17H), 8.30(s, 1H), 8.36 (d, J=9Hz, 1H).

IR (KBr): 3350, 2930, 2850, 1780, 1720, 1680, 1620, 1510, 1440, 1360, 1300, 1240, 1220, 1170, 1030, 950, 905, 820, 750, 700 m$^{-1}$.

The compound (0.20 g) was obtained by the said reaction was dissolved in THF (5 ml) and stirred at 50° C. for 15 minutes by addition of 50% aqueous formic acid (3 ml). The reaction solution was concentrated under reduced pressure, then trifluoroacetic acid (5 ml) was added to the residue and it was stirred at room temperature for 30 minutes. The reaction solution was concentrated under reduced pressure and then the residue was cleansed with ether thereby a yellow powder product was obtained. This one was dissolved in aqueous sodium bicarbonate solution and purified by HP-20 column chromatography thereby sodium 7-[(Z)-2-(2-aminothiazol-4-yl)-2-hydroxyiminoacetamido]-3-[(Z)-2-(1,2,3-thiadiazol-4-yl)vinyl]-3-cephem-4-carboxylate (10 mg) was obtained.

due was cleansed with ether thereby a yellow powder product was obtained. This one was dissolved in aqueous sodium bicarbonate solution and purified by HP-20 column chromatography thereby sodium 7-[(Z)-2-(2-aminothiazol-4-yl)-2-hydroxyiminoacetamido]-3-[(Z)-2-(1,2,3-thiadiazol-4-yl)vinyl]-3-cephem-4-carboxylate (15 mg) was obtained.

EXAMPLE 8

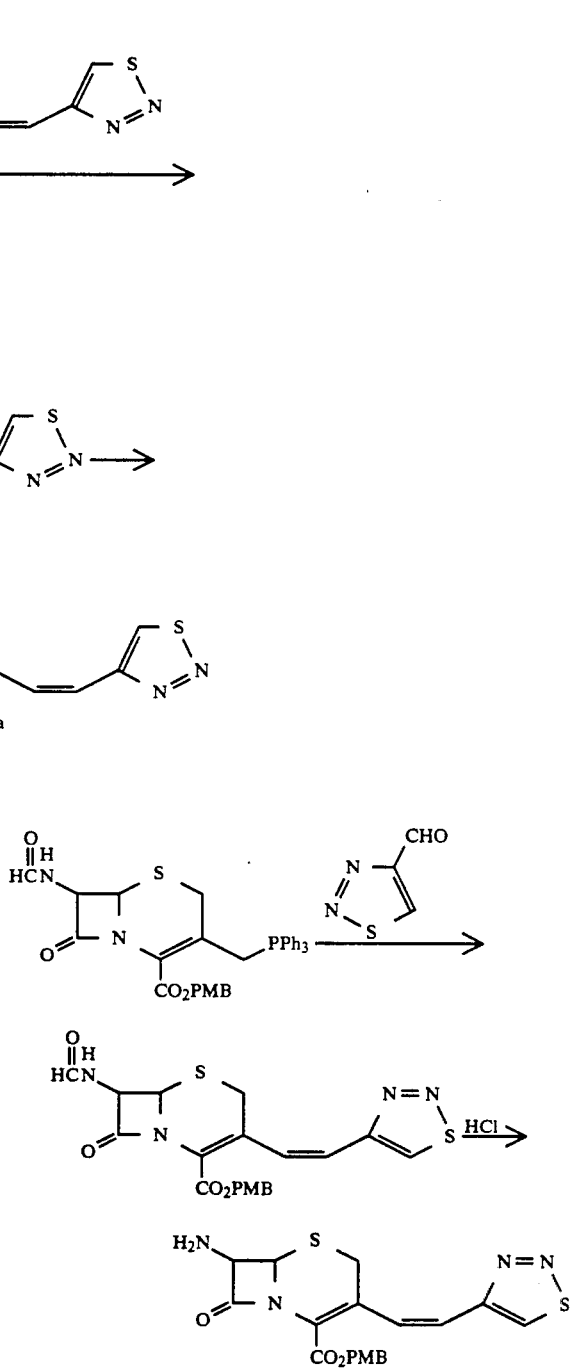

Crude p-methoxybenzyl 7-formylamino-3-triphenylphosphoranilidene-methyl-3-cephem-4-carboxylate (3 g) prepared by following the procedure of Referential Example 1, using, as starting material, [7-formylamino-4-(4-methoxybenzyloxycarbonyl)-3-cephem-3-ylmethyl]triphenylphosphonium iodide (4.5 g, 5.9 mol), was dissolved in methylene chloride (20 ml) and 4-formyl-1,2,3-thiadiazol (1 g, 8.8 mmol) was added. It was stirred overnight at room temperature, the solvent was distilled off under reduced pressure and it was purified by silica gel column chromatography thereby p-methoxybenzyl 7-formylamino-3-[(Z)-2-1,2,3-thiadiazol-4-yl)vinyl]-3-cephem-4-carboxylate (0.6 g) was obtained as a yellow powder solid.

$^1$H-NMR (DMSO-d$_6$) δ: 3.68 (q$_{AB}$, J=18Hz, 2H), 3.78 (s, 2H), 5.03 (s, 2H), 5.27 (d, J=5Hz), 1H), 5.86 (dd, J=9Hz, J=5Hz, 1H), 6.72 (d, J=12Hz, 1H), 6.92 (d, J=9Hz, 2H), 6.97 (d, J=12Hz, 1H), 7.28 (d, J=9Hz, 2H), 8.18 (s, 1H), 9.04 (s, 1H), 9.13 (d, J=9Hz, 1H).

The said ester (0.6 g, 1.3 mmol) was dissolved in methanol (10 ml). It was stirred at room temperature for 2 hours by addition of concentrated hydrochloric acid (0.1 ml). After the solvent was distilled off, a small amount of water was added to the residue, and aqueous saturated sodium bicarbonate solution was added to adjust to pH 8–9. It was dissolved by addition of ethyl acetate, and the organic layer was separated. The organic layer was dried, the solvent was distilled off and the residue was purified by silica gel column chromatography thereby p-methoxybenzyl 7-amino-3-[(Z)-2-(1,2,3-thiadiazol-4-yl)vinyl]-3-cephem-4-carboxylate (0.21 g) was obtained as a yellow powder solid.

$^1$H-NMR (DMSO-d$_6$) δ: 3.68 (q$_{AB}$, J=18Hz, 2H), 3.77 (s, 2H), 5.03 (s, 2H), 5.16 (d, J=5Hz, 1H), 6.68 (d, J=12Hz, 1H), 6.93 (d, J=9Hz, 2H), 6.96 (d, J=12Hz, 1H), 7.28 (d, J=9Hz, 2H), 9.03 (s, 1H).

EXAMPLE 9

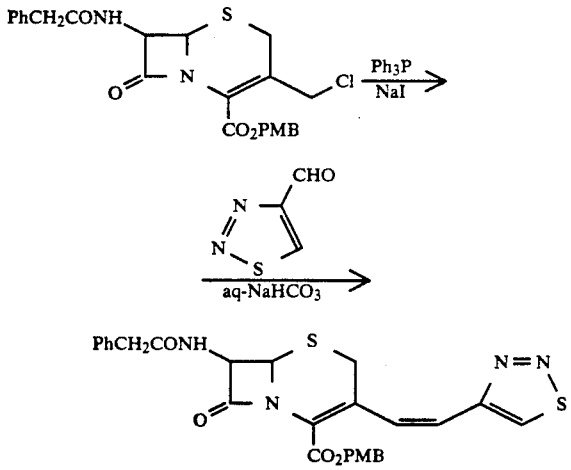

Triphenyl phosphine (5.8 g, 22 mmol) was added to a DMF (50 ml) solution of p-methoxybenzyl 7-phenylacetamido-3-chloromethyl-3-cephem-4-carboxylate (10 g, 20 mmol) and sodium iodide (3.3 g, 22 mmol) and the mixture was stirred at room temperature for 2 hours. The reaction solution was added in isopropyl alcohol-diisopropyl ether (1:1, 2000 ml). Precipitates were collected by filtration and then dried under reduced pressure thereby a white crystal compound was obtained. This compound was dissolved in methylene chloride (30 ml), then 4-formyl-1,2,3-thiazole (2.7 g, 24 mmol) was added, and it was stirred at room temperature for 18 hours by addition of aqueous saturated sodium bicarbonate solution (30 ml). The reaction solution was separated and then the methylene chloride layer was washed with water. It was dried over magnesium sulfate and the solvent was distilled off thereby the residue was obtained. It was purified by column chromatography thereby p-methoxybenzyl 7-phenylacetamido-3-[(Z)-2-(1,2,3-thiadiazol-4-yl)vinyl]-3-cephem-4-carboxylate (7.6 g, 70% yield) was obtained as a white powdered substance.

$^1$H-NMR (CDCl$_3$) δ: 3.48 (d, J=18Hz, 1H), 3.73 (d, J=18Hz, 1H), 3.77 (s, 3H), 5.05 (d, J=5Hz, 2H), 5.25 (d, J=5Hz, 1H), 5.79 (dd, J=5Hz, J=8Hz, 1H), 6.70 (d, J=12Hz, 1H), 6.92 (d, J=9Hz, 2H), 6.98 (d, J=12Hz, 1H), 7.40 (d, J=9Hz, 2H), 7.42 (s, 5H), 9.03 (s, 1H), 9.17 (d, J=8Hz, 1H).

IR (KBr): 3300, 3050, 2970, 1770, 1665, 1620, 1540, 1520, 1380, 1360, 1300, 1250, 1180, 1100, 1030, 980, 825, 700, 540 m$^{-1}$.

EXAMPLE 10

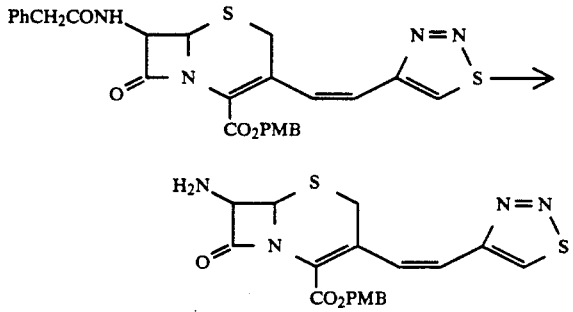

Phosphorus pentachloride (8.12 g, 39 mmol) was added to methylene chloride (70 ml) and cooled to 5° C. It was stirred for 1 hour by addition of pyridine (10.39 g, 130 mmol). p-Methoxybenzyl 7-phenylacetamido-3-[(Z)-2-(1,2,3-thiadiazol-4-yl)vinyl]-3-cephem-4-carboxylate (7.27 g, 13 mmol) was added to this reaction solution and it was stirred at 5° C. for 4 hours. The reaction solution was cooled to −30° C. and stirred for 1 hour by addition of dehydrated methanol (53 ml). The temperature of the reaction solution was returned to −10° C. and it was stirred for 10 minutes by addition of water (10 ml). Saturated sodium bicarbonate was added to the reaction solution to adjust to pH 4, and then the solvent was distilled off under reduced pressure. The residue was extracted with ethyl acetate, then washed with water and dried over magnesium sulfate. The solvent was distilled off and the residue was purified by column chromatography thereby p-methoxybenzyl 7-amino-3-[(Z)-2-(1,2,3-thiadiazol-4-yl)vinyl]-3-cephem-4-carboxylate (3.9 g, 70% yield) was obtained as a light yellow powder substance.

EXAMPLE 11

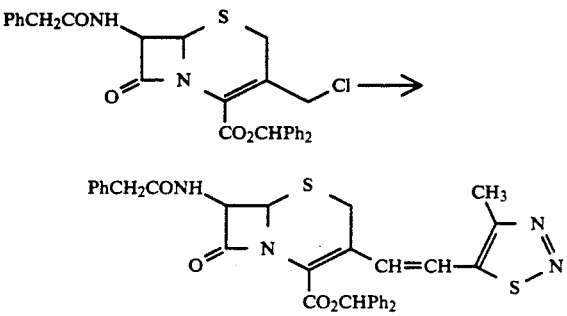

Triphenyl phosphine (6.9 g, 26.4 mmol) and sodium iodide (3.96 g, 26.4 mmol) were added to a DMF (32 ml) solution of benzyhydryl 7-phenyl-acetamido-3-chloromethyl-3-cephem-4-carboxylate (12.8 g, 24 mmol) and the mixture was stirred at room temperature for 3 hours. The reaction solution was added in ethyl acetate (500 ml). Precipitates were collected by filtration and then dried thereby a white crystal compound (21.56 g) was obtained. This compound (17.72 g) was dissolved in methylene chloride (30 ml), then 5-formyl-4-methyl-1,2,3-thiadiazole (2.49 g, 19.4 mmol) was added, aqueous saturated sodium bicarbonate solution (30 ml) was further added and stirred at room temperature for 3 hours. The reaction solution was separated and the methylene chloride layer was washed with water. It was dried over magnesium sulfate, then the solvent was distilled off and after that, the residue was purified by column chromatography thereby a 3-double bonded isomer of benzhydryl 7-phenylacetamido-3-[2-(4-methyl-1,2,3-thiadiazol-5-yl)vinyl]-3-cephem-4-carboxylate (E/Z=1/3.5, 5.69 g, 47% yield) was obtained.

$^1$H-NMR (CDCl$_3$, 1:3.5 mixture of E and % isomers) δ: 2.50 and 2.56 (s, 3H), 3.20 (q$_{AB}$, J=18Hz, 2H), 3.60 (s, 2H), 4.96 and 5.03 (d, J=4.5Hz, 1H), 5.89 (dd, J=4.5Hz, J=9Hz, 1H), 6.33 (d, J=12Hz, 1H), 6.53 (d, J=12Hz, 1H), 6.76 (s, 1H), 7.13-7.26 (m, 15H).

IR (KBr): 3300, 3050, 1790, 1730, 1680, 1530, 1380, 1220, 1180, 1090, 1005, 740 700 m$^{-1}$.

EXAMPLE 12

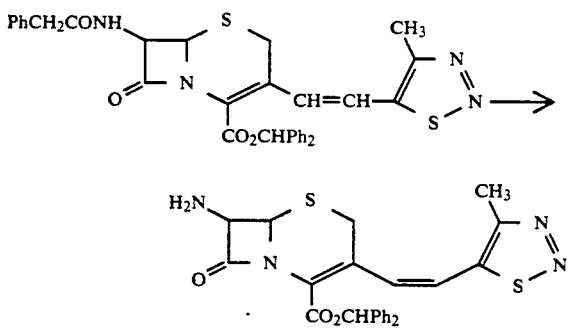

Phosphorus pentachloride (5.83 g, 28 mmol) was made a methylene chloride (50 ml) suspension, pyridine (7.39 g, 93 mmol) was added at 5°–10° C. and stirring was continued for 40 minutes. Added all at once at 5° C. thereto was benzhydryl 7-phenylacetamido-3-[2-(4-methyl-1,2,3-thiadiazol-5-yl)vinyl]-3-cephem-4-carboxylate (E/Z=1/3.5, 5.69 g, 9.36 mmol), and the mixture was stirred at the same temperature for 3 hours. Methanol (38 ml) was slowly added to the reaction mixture at −50° C., and it was stirred for 1 hour at −50° to −30° C. Water (7 ml) was added at −10° C. and the reaction temperature was set at 0° C. and then it was stirred for 10 minutes. The reaction solution was adjusted to pH 6 with saturated sodium bicarbonate solution and then extracted with methylene chloride. It was washed with water and then the methylene chloride layer was dried over magnesium sulfate. The solvent was distilled off and then ethyl acetate was added to the residue. Precipitates were filtered and then cleansed with ethyl acetate thereby benzhydryl 7-amino-3-[(Z)-2-(4-methyl-1,2,3-thiadiazol-5-yl)vinyl]-3-cephem-4-carboxylate (2.06 g, 45% yield) was obtained.

$^1$H-CDCl$_3$-d$_6$DMSO δ: 2.50 (s, 3H), 2.80 (bs, 2H), 3.46 (q$_{AB}$, J=18Hz, 2H), 4.89 (d, J=3Hz, 1H), 5.10 (d, J=3Hz, 1H), 6.36 (d, J=12Hz, 1H), 6.59 (d, J=12Hz, 1H), 6.76 (s, 1H), 7.17-7.26 (m, 10H).

IR (KBr): 3245, 2960, 1765, 1720, 1600, 1390, 1370, 1290, 1220, 1100, 1005, 760, 700 cm$^{-1}$.

EXAMPLE 13

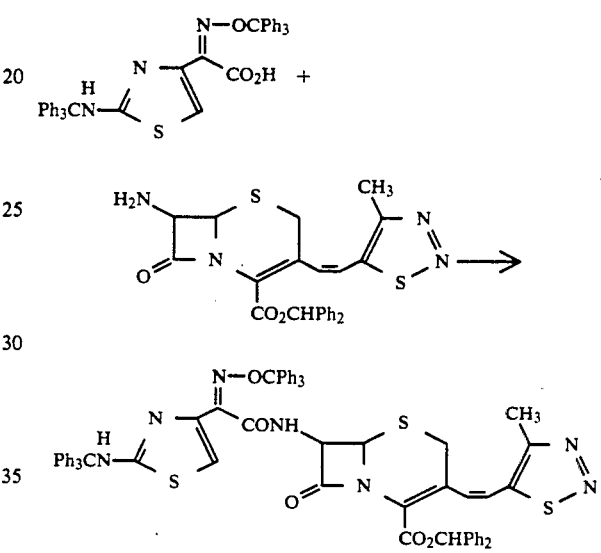

(Z)-2-(2-tritylaminothiazol-4-yl)-2-trityloxyiminoacetic acid (1.58 g, 2.35 mmol) was dissolved in a mixed solvent of THF-methylene chloride (20 ml-10 ml) and cooled to 5° C. HOBT (0.32 g, 2.4 mmol) was added to this reaction solution, then DCC (0.50 g, 2.4 mmol) was added and the mixture was stirred at the same temperature for 2 hours. The reaction solution was filtered, then benzhydryl 7-amino-3-[(Z)-2-(4-methyl-1,2,3-thiadiazol-5-yl)vinyl]-3-cephem-4-carboxylate (0.98 g, 2.0 mmol) was added to the filtrate and it was stirred at 5° C. for 22 hours. The reaction solution was concentrated and then the concentrate was purified by column chromatography thereby benzhydryl 7-[(Z)-2-(2-tritylaminothiazol-4-yl)-2-trityloxyiminoacetamido]-3-[(Z)-2-(4-methyl-1,2,3-thiadiazol-5-yl)vinyl]-3-cephem-4-carboxylate (1.38 g, 60.5% yield) was obtained as a yellow powdered compound.

$^1$H-NMR (CDCl$_3$) δ: 2.50 (s, 3H), 3.10 (q$_{AB}$, J=18Hz, 2H), 5.13 (d, J=4.5Hz, 1H), 6.16 (dd, J=4.5Hz, J=9Hz, 1H), 6.39 (s, 1H), 6.43 (d, J=12Hz, 1H), 6.80 (s, 1H), 7.10-7.40 (m, 40H).

IR (KBr): 3400, 3075, 3025, 1790, 1730, 1530, 1500, 1440, 1220, 960, 750, 700 cm$^{-1}$.

EXAMPLE 14

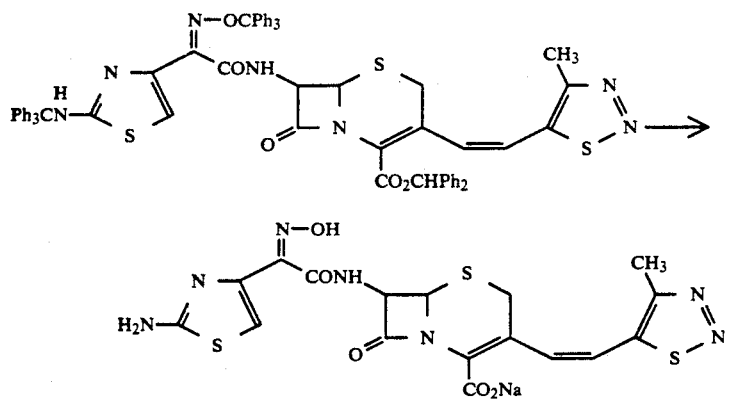

Benzhydryl 7-[(Z)-2-(2-tritylaminothiazol-4-yl)-2-trityloxyiminoacetamido]-3-[(Z)-2-(4-methyl-1,2,3-thiadiazol-5-yl)vinyl]-3-cephem-4-carboxylate (1.38 g, 1.2 mmol) was stirred at room temperature for 1 hour by addition of formic acid (14 ml). Concentrated hydrochloric acid (0.11 ml) was added to the reaction solution and the mixture was stirred at room temperature for 1 hour. The reaction solution was concentrated under reduced pressure and the residue was cleansed with ether thereby a yellow powder product was obtained. This one was dissolved in aqueous sodium bicarbonate solution and purified by HP-20 column chromatography thereby sodium 7-[(Z)-2-(2-aminothiazol-4-yl)-2-hydroxyiminoacetamido]-3-[(Z)-2-(4-methyl-1,2,3-thiadiazol-5-yl)vinyl]-3-cephem-4-carboxylate (79 mg) was obtained.

$^1$H-NMR (D$_2$O) δ: 2.55 (s, 3H), 3.39 (q$_{AB}$, J=18Hz, 2H), 5.36 (d, J=5Hz, 1H), 5.84 (d, J=5Hz, 1H), 6.57 (d, J=11Hz, 1H), 6.61 (d, J=11Hz, 1H), 6.91 (s, 1H).

IR (KBr): 3425, 1765, 1665, 1600, 1540, 1390, 1360 cm$^{-1}$.

EXAMPLE 15

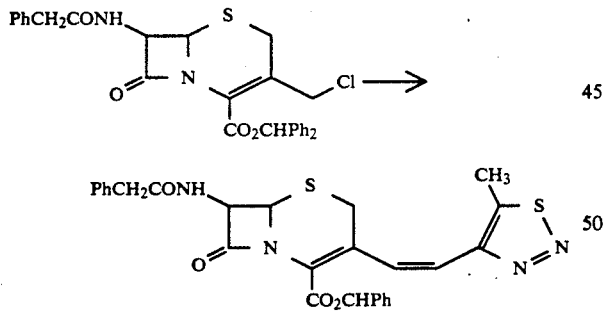

Triphenyl phosphine (21.7 g, 83 mmol) and sodium iodide (12.4 g, 83 mmol) were added to a DMF (100 ml) solution of benzhydryl 7-phenylacetamido-3-chloromethyl-3-cephem-4-carboxylate (40 g, 75 mmol), and the mixture was stirred at room temperature for 2.5 hours. The reaction solution was added in ethyl acetate and precipitates were collected by filtration. The precipitates were cleansed with ethyl acetate and then dried thereby a white crystal compound (74.62 g) was obtained. This compound (29.3 g, 33 mmol) was dissolved in methylene chloride (70 ml), 4-formyl-5-methyl-1,2,3-thiadiazole (4.23 g, 33 mmol) was added, aqueous saturated sodium bicarbonate solution (49.5 ml) was further added and the mixture was stirred at room temperature for 1 hour and 10 minutes. The reaction solution was separated and the methylene chloride layer was washed with water. It was dried over magnesium sulfate and the solvent was distilled off thereby the residue was obtained. It was purified by column chromatography thereby a 3-double bonded isomer of benzhydryl 7-phenylacetamido-3-[(2-(5-methyl-1,2,3-thiadiazol-4-yl)vinyl]-3-cephem-4-carboxylate (E/Z=1,2,3, 6.21 g, 45% yield) was obtained.

$^1$H-NMR (CDCl$_3$, 1:2.3 mixture of E and Z isomers) δ: 2.50 and 2.55 (s, 3H), 3.57 (q$_{AB}$, J=18Hz, 1H), 3.73 (s, 2H), 5.18 (d, J=4.5Hz, 1H), 5.90 (dd, J=4.5Hz, J=9Hz, 1H), 6.45 (d, J=12Hz, 1H), 6.92 (s, 1H), 7.05 (d, J=12Hz, 1H), 7.28–7.60 (m, 15H).

IR (KBr): 3300, 1780, 1725, 1670, 1530, 1500, 1370, 1310, 1295, 1240, 1215, 1175, 1085, 1005, 755, 740, 700 cm$^{-1}$.

EXAMPLE 16

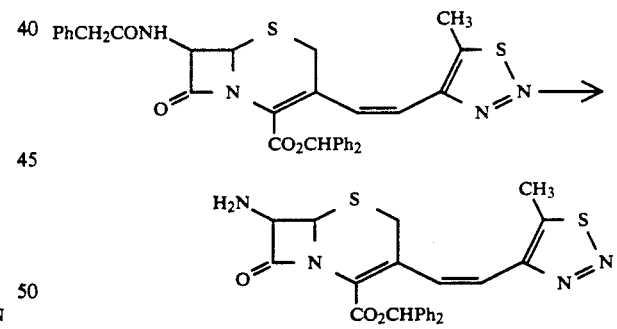

Phosphorus pentachloride (4.23 g, 20.3 mmol) was made a methylene chloride (38 ml) suspension, pyridine (5.35 g, 67.7 mmol) was added at 5° to 10° C. and it was stirred for 1 hour. Added all at once at 5° C. thereto as benzhydryl 7-phenylacetamido-3-[2-(5-methyl-1,2,3-thiadiazol-4-yl)vinyl]-3-cephem-4-carboxylate (E/Z=1/2.3, 4.12 g, 6.8 mmol), and the mixture was stirred at the same temperature for 2 hours. The reaction solution was cooled to −78° C., then methanol (28 ml) was added and after that, the reaction temperature was returned to −30° C. and stirring was effected for 1 hour. Further, the reaction temperature was returned to −10° C., then water (5 ml) was added and stirring was effected for 20 minutes. The reaction solution was adjusted to pH 7 with aqueous saturated sodium bicarbonate solution and then extracted with methylene chloride. It was washed with water and then the methylene chloride layer was dried over magnesium sulfate. After the solvent was distilled off, the residue was purified by column chromatography thereby benzhydryl 7-amino-3-[(Z)-2-(5-methyl-1,2,3-thiadiazol-4-yl)vinyl]-4-cephem-4-carboxylate (1.5 g, 45% yield) was obtained.

¹H-NMR (CDCl₃-d₆DMSO) δ: 1.75 (s, 2H), 2.31 (s, 3H), 3.52 (d, J=16Hz, 2H), 4.80 (d, J=4.5Hz, 1H), 5.10 (d, J=4.5Hz, 1H), 6.38 (d, J=12Hz, 1H), 6.85 (d, J=12Hz, 1H), 6.93 (s, 1H), 7.10-7.60 (m, 10H).

IR (KBr): 3415, 1765, 1720, 1365, 1240, 1214, 1170, 1080, 740, 695 cm⁻¹.

EXAMPLE 17

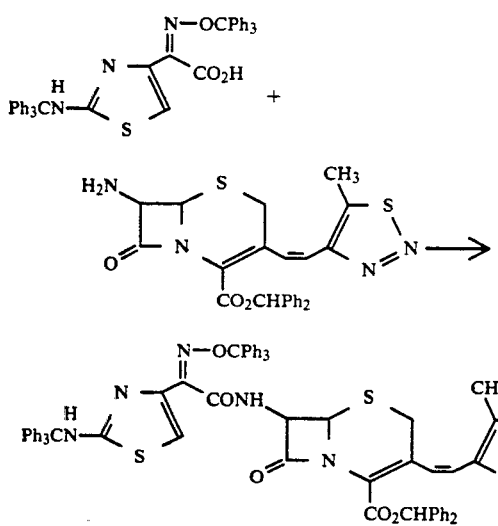

(Z)-2-(2-tritylaminothiazol-4-yl)-2-trityloxyiminoacetic acid (1.17 g, 1.7 mmol) was dissolved in THF (15 ml) and cooled to 5° C. HOBT (0.27 g, 1.9 mmol) and then DCC (0.36 g, 1.7 mmol) were added to this reaction solution was stirred at the same temperature for 2 hours. The reaction solution was filtered, then benzyhydryl 7-amino-3-[(Z)-2-(5-methyl-1,2,3-thiadiazol-4-yl)vinyl]-3-cephem-4-carboxylate (0.85 g, 1.7 mmol) was added to this filtrate and it was stirred at 5° C. for 2 days. The reaction solution was concentrated, then the concentrate was purified by column chromatography thereby benzhydryl 7-[(Z)-2-(2-tritylaminothiazol-4-yl)-2-trityloxyiminioacetamido]-3-[(Z)-2-(5-methyl-1,2,3-thiadiazol-4-yl)vinyl]-3-cephem-4-carboxylate (1.17 g, 59% yield) was obtained as a yellow powdered compound.

¹H-NMR (CDCl₃) δ: 2.43 (s, 3H), 3.41 (q$_{AB}$, J=18Hz, 2H), 5.22 (d, J=4.5Hz, 1H), 6.12 (dd, J=4.5Hz, J=9Hz, 1H), 6.42 (d, J=12Hz, 1H), 6.82 (d, J=12Hz, 1H), 6.89 (s, 1H), 7.15-7.50 (m, 40H).

EXAMPLE 18

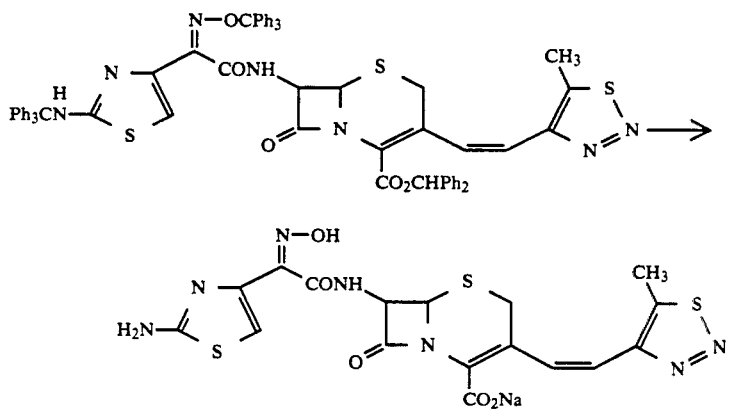

Benzhydryl 7-[(Z)-2-(2-tritylaminothiazol-4-yl)-2-trityloxyiminoacetamido]-3-[(Z)-2-(5-methyl-1,2,3-thiadiazol-4-yl)vinyl]-3-cephem-4-carboxylate (0.5 g, 0.4 mmol) was stirred at room temperature for 2 hours by addition of formic acid (5 ml). Concentrated hydrochloric acid (40 μl) was added to the reaction solution and it was stirred at room temperature for 1 hour. The reaction solution was concentrated under reduced pressure and then the residue was cleansed with ether thereby a powdered product was obtained. This one was dissolved in aqueous sodium bicarbonate solution and purified by HP-20 column chromatography thereby sodium 7-[(Z)-2-(2-aminothiazol-4-yl)-2-hydroxyiminoacetamido]-3-[(Z)-2-(5-methyl-1,2,3-thiadiazol-4-yl)vinyl]-3-cephem-4-carboxylate (0.13 g) was obtained.

¹H-NMR (D₂O) δ: 2.46 (s, 3H), 3.27 (q$_{AB}$, J=17Hz, 2H), 5.17 (d, J=4.5Hz, 1H), 5.71 (d, J=4.5Hz, 1H), 6.52 (d, J=12Hz, 1H), 6.65 (d, J=12Hz, 1), 6.80 (s, 1H),

IR (KBr): 3400, 1760, 1665, 1610, 1535, 1390, 1355 cm⁻¹.

EXAMPLE 19

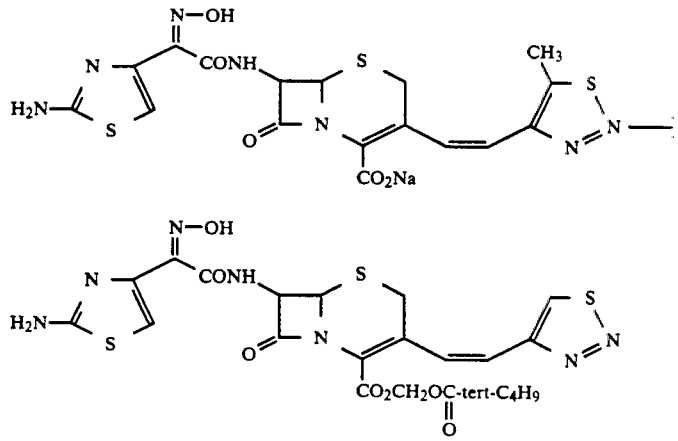

Sodium 7-[(Z)-2-(2-aminothiazol-4-yl)-2-hydroxyiminoacetamido]-3-[(Z)-2-(1,2,3-thiadiazol-4-yl)vinyl]-

3-cephem-4-carboxylate (0.20 g, 0.39 mmol) was dissolved in DMF (2 ml) and methyl pivalate iodide (0.19 g, 0.8 mmol) was added under ice-cooling. The reaction solution was stirred for 15 minutes under ice-cooling, then water (30 ml) was added and it was extracted with ethyl acetate (30 ml). The organic layer was washed with water and then dried over magnesium sulfate.

After the solvent was distilled off, the residue was pulverized in diethyl ether thereby pivalyloxymethyl 7-[(Z)-(2-aminothiazol-4-yl)-2-hydroxyiminoacetamido]-3-[(Z)-2-(1,2,3-thiadiazol-4-yl)vinyl]-3-cephem-4-carboxylate (0.08 g) was obtained.

$^1$H-NMR (CDCl$_3$) δ: 1.18 (s, 9H), 3.42 and 3.62 (q$_{AB}$, J=18Hz, 2H), 5.21 (d, J=5Hz, 1H), 5.45 (bs, 2H), 5.80 (d, J=5Hz, 1H), 5.91 (d, J=5Hz, 1H), 5.98 (d, J=5Hz, J=9Hz, 1H), 6.00 (d, J=12Hz, 1H), 6.84 (d, J=12Hz, 1H), 7.14 (s, 1H), 8.40 (s, 1H), 11.06 (bs, 1H).

IR (KBr): 3300, 2980, 1780, 1750, 1710, 1660, 1520, 1360, 1220, 1120, 980, 800 cm$^{-1}$.

EXAMPLE 20

J=12Hz, 1H), 6.79 (d, J=10Hz, 2H), 7.21 (d, J=10Hz, 1H), 8.29 (s, 1H), 8.50 (s, 1H), 8.81 (d, J=10Hz, 1H).

Said ester (1.35 g, 2.9 mmol) was dissolved in ethanol (25 ml), concentrated hydrochloric acid (0.25 ml) was added and the mixture was stirred for 6 hours under ice-cooling and for 1 hour at room temperature. The reaction solution was concentrated under reduced pressure, then saturated sodium bicarbonate solution was added to the residue and it was extracted with methylene chloride. It was washed with water and then dried over magnesium sulfate. The solvent was distilled off and the residue was purified by column chromatography thereby p-methoxybenzyl 7-amino-3-[(Z)-2-(1,2,3-thiadiazol-4-yl)vinyl]-3-cephem-4-carboxylate (0.58 g, 45% yield) was obtained.

$^1$H-NMR (DMSO-d$_6$) δ: 3.74 (s, 3H), 4.97 (s, 2H), 5.00 (d, J=5Hz, 1H), 5.26 (d, J=5Hz, 1H), 6.50 (d, J=12Hz, 1H), 6.76 (d, J=12Hz, 1H), 6.82 (d, J=10Hz, 2H), 7.13 (d, J=10Hz, 2H), 8.84 (s, 1H).

EXAMPLE 21

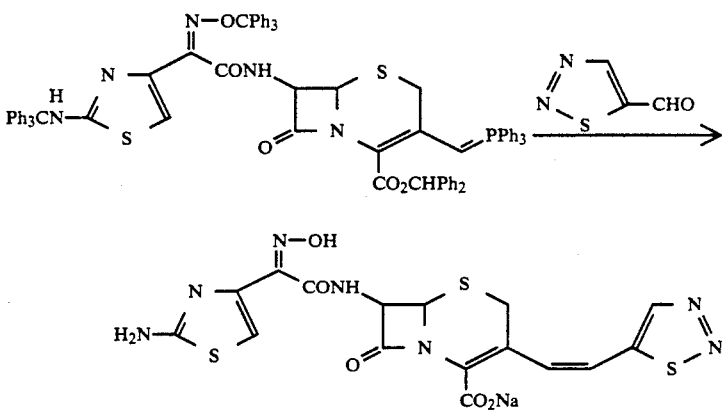

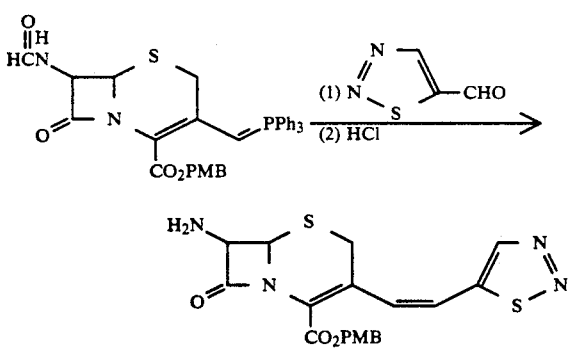

5-Formyl-1,2,3-thiadiazole (0.47 g, 4.1 mmol) was added to a methylene chloride (42 ml) solution of p-methoxybenzyl 7-formylamino-3-triphenylphosphoranilidenemethyl-3-cephem-4-carboxylate (2.8 g, 4.5 mmol) and the mixture was stirred at room temperature for 1.5 hours. The reaction solution was concentrated under reduced pressure and the residue was purified by column chromatography thereby p-methoxybenzyl 7-formylamino-3-[(Z)-2-(1,2,3-thiadiazol-4-yl)vinyl]-3-cephem-4-carboxylate (0.37 g, 20% yield) was obtained.

$^1$H-NMR (CDCl$_3$) δ: 3.25 (q$_{AB}$, J=18Hz, 2H), 3.70 (s, 3H), 5.07 (s, 2H), 5.13 (d, J=5Hz, 1H), 5.97 (dd, J=5Hz, J=10Hz), 6.50 (d, J=12Hz, 1H), 6.76 (d,

Diphenylmethyl 7-[(Z)-2-(2-tritylaminothiazol-4-yl)-2-trityloxyiminoacetamido]-3-[(triphenylphosphoranilidene)methyl]-3-cephem-4-carboxylate [Japanese Laid-open Patent Application No. 491/1987] (3.1 g, 2.9 mmol) was dissolved in ethyl acetate, 5-formyl-1,2,3-thiadiazole (0.35 g, 3.1 mmol) was added and the mixture was stirred at room temperature for 2.5 hours. The reaction solution was concentrated under reduced pressure and then the residue was purified by column chromatography thereby benzhydryl 7-[(Z)-2-(2-tritylaminothiazol-4-yl)-2-trityloxyiminoacetamido]-3-[(Z)-2-(1,2,3-thiadiazol-5-yl)vinyl]-3-cephem-4-carboxylate (0.67 g, 26% yield) was obtained.

$^1$H-NMR (CDCl$_3$) δ: 3.44 (m, 2H), 5.04 (d, J=5Hz, 1H), 6.05 (dd, J=5Hz, J=9Hz, 1H), 6.48 (s, 1H), 6.91 (s, 1H), 6.94 (d, J=12Hz, 1H), 7.1-7.7 (m, 41H), 8.33 (s, 1H).

Said ester (0.67 g, 0.74 mmol) was stirred at room temperature for 1 hour by addition of formic acid (8.5 ml), then concentrated hydrochloric acid (0.75 ml) was added to the reaction solution and the mixture was stirred at room temperature for 4 hours. The reaction solution was concentrated under reduced pressure, then sodium bicarbonate was added to the residue to adjust to pH 7.4 and then the solution was purified by HP-20 column chromatography thereby sodium 7-[(Z)-2-(2-aminothiazol-4-yl-2-hydroxyiminoacetamido]-3-[(Z)-2-(1,2,3-thiadiazol-5-yl)vinyl]-3-cephem-4-carboxylate (14 mg) was obtained.

$^1$H-NMR (D$_2$O) δ: 3.27 (d, J=18Hz, 1H), 3.55 (d, J=18Hz, 1H), 5.38 (d, J=5Hz, 1H), 5.85 (d, J=5Hz, 1H), 6.58 (d, J=11Hz, 1H), 6.77 (d, J=11Hz, 1H), 6.90 (s, 1H), 8.67 (s, 1H).

EXAMPLE 22

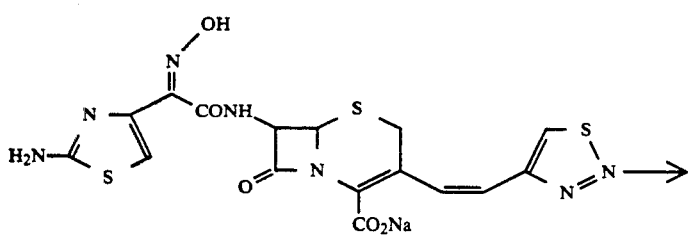

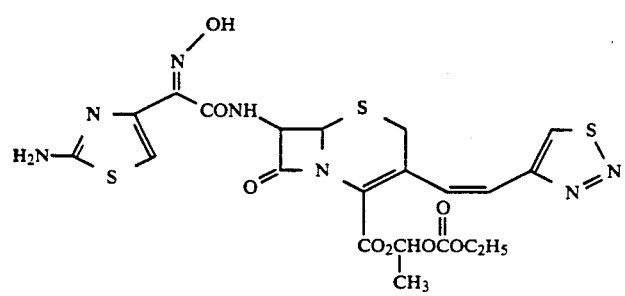

In like manner as in Example 20 sodium 7-[(Z)-(2-aminothiazol-4-yl)-2-hydroxyiminoacetamido]-3-[(Z)-2-(1,2,3-thiadiazol-4-yl)vinyl]-3-cephem-4-carboxylate (1 g) was reacted with DL-1-iodoethyl-4-ethylcarbonate (0.5 g) thereby DL-1-ethoxycarbonyloxyethyl 7-[(Z)-(2-aminothiazol-4-yl)-2-hydroxyiminoacetamido]-3-[(Z)-2-(1,2,3-thiadiazol-4-yl)vinyl]-3-cephem-4-carboxylate (0.7 g) was obtained.

$^1$H-NMR (CDCl$_3$) δ: 1.32 (t, J=7Hz, 3H), 1.55 (d, J=5Hz, 3H), 3.42, 3.66 (q$_{AB}$, J=18Hz, 2H), 4.22 (m, 2H), 5.21 (d, J=5Hz, 1H), 5.62 (bs, 1H), 5.97 (dd, J=5Hz, 9Hz, 1H), 6.80-6.97 (m, 3H), 7.04 (s, 1H), 8.42 (s, 1H), 10.86 (d, J=9Hz, 1H).

IR (KBr, disc.): 3340, 3000, 1750, 1610, 1530, 1380, 1265, 1220, 1070, 995, 860, 795 cm$^{-1}$.

EXAMPLE 23

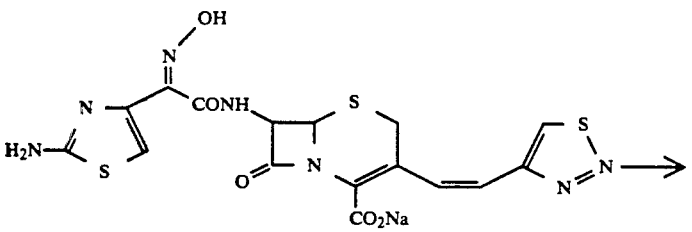

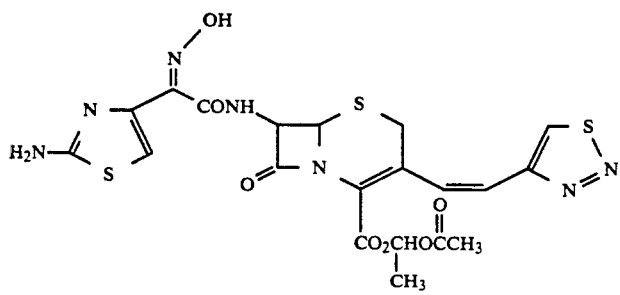

In like manner as in Example 20 sodium 7-[(Z)-2-(2-aminothiazol-4-yl)-2-hydroxyiminoacetamido]-3-[(Z)-2-(1,2,3-thiadiazol-4-yl)vinyl]-3-cephem-4-carboxylate (0.5 g) was reacted with DL-2-bromoethyl acetate (0.23 g) thereby DL-1-acetyloxyethyl 7-[(Z)-2-(2-aminothiazol-4-yl)-2-hydroxyiminoacetamido]-3-[(Z)-2-(1,2,3-thiadiazol-4-yl)vinyl]-3-cephem-4-carboxylate (0.13 g) was obtained.

$^1$H-NMR (DMSO-d$_6$) δ: 1.32, 1.38 (d, J=6Hz, 3H), 2.04 (s, 3H), 3.48, 3.65, 3.67 (q$_{AB}$, J=18Hz, 2H), 5.27, 5.29 (d, J=5Hz, 1H), 5.86 (dd, J=5Hz, 8Hz, 1H), 6.65, 6.66 (d, J=12Hz, 2H), 6.73, 6.82 (q, J=5Hz, 1H), 6.94, 6.97 (d, J=12Hz, 2H), 7.10 (s, 1H), 9.03, 9.04 (s, 1H), 9.47 (d, J=8Hz), 11.29 (s, 1H).

IR (KBr, disc.): 3400, 3000, 1765, 1675, 1620, 1530, 1370, 1210, 1070, 1000, 940 cm$^{-1}$.

EXAMPLE 24 (FORMULATION EXAMPLE)

| Tablet | |
|---|---|
| Product obtained in Example 23 | 175 mg |
| Lactose | 16 mg |
| Starch | 5 mg |
| Hydroxyethyl cellulose | 3 mg |

| Tablet | |
|---|---|
| Magnesium stearate | 1 mg |
| | (200 mg/1 tablet) |

The product obtained in Example 23 and lactose were blended. Thereafter, the mixture was kneaded with hydroxyethyl cellulose, dried and pulverized. To the resulting pulverized mixture was added magnesium stearate which had been dispersed in starch in advance. The mixture was tableted in a customary manner to form tablets.

What we claim is:

1. A cephalosporin compound of the formula

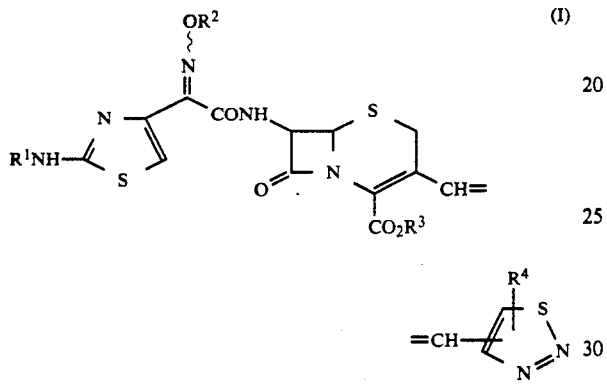

in which $R^1$ is a hydrogen atom or a protective group for the amino group, $R^2$ is a hydrogen atom or a protective group for the hydroxyl group, $R^3$ is a hydrogen atom, a salt-forming cation or a protective group for the carboxyl group, and $R^4$ is a hydrogen atom, a halogen atom or a lower alkyl group, or a pharmacologically acceptable salt thereof.

2. A pharmaceutical composition comprising an antibacterially effective amount of a cephalosporin compound or a pharmacologically acceptable salt thereof as defined in claim 1 and a pharmacologically acceptable carrier therefor.

3. A method for the prevention or the treatment of a bacterial infectious disease in a patient which comprises administering to the patient an antibacterially effective amount of a cephalosporin compound or a pharmacologically acceptable salt thereof as defined in claim 1.

4. A compound of claim 1 in which $R^1$ is a hydrogen atom.

5. A compound of claim 1 in which $R^2$ is a hydrogen atom.

6. A compound of claim 1 in which $R^3$ is hydrogen or a methyl, ethyl, allyl, tert-butoxycarbonylmethyl, 2-tert-butoxycarbonylethyl, 2,2,2-trichloroethyl, acetoxymethyl, propionyloxymethyl, pivaloyloxymethyl, 1- or 2-acetoxyethyl, 1- or 2-pivaloyloxyethyl, methoxycarbonyloxymethyl, ethoxycarbonyloxymethyl, tert-butoxycarbonyloxymethyl, 1- or 2-ethoxycarbonyloxyethyl, 1- or 2-tert-butoxycarbonyloxyethyl, benzyl, 4-methoxybenzyl or diphenylmethyl group.

7. A compound of claim 1 in which $R^4$ is a hydrogen atom or a methyl group.

8. A compound of claim 1 being of a syn form or being based on the syn form.

9. A compound of claim 1 being a (Z)-isomer.

10. A compound of claim 1 being in a form of a pharmacologically acceptable salt.

11. A compound of claim 1 being 7-[(Z)-2-(2-aminothiazol-4-yl)-2-hydroxyiminoacetamido]-3-[(Z)-2-(1,2,3-thiadiazol-4-yl)vinyl]-3-cephem-4-carboxylic acid and its 1-ethoxycarbonyloxyethyl ester or 1-acetoxyethyl ester, 7-[(Z)-2-(2-aminothiazol-4-yl)-2-hydroxyiminoacetamido]-3-[(Z)-2-(4-methyl-1,2,3-thiadiazol-5-yl)vinyl]-3-cephem-4-carboxylic acid, 7-[(Z)-2-(2-aminothiazol-4-yl)-2-hydroxyiminoacetamido]-3-[(Z)-2-(5-methyl-1,2,3-thiadiazol-4-yl)vinyl(-3-cephem-4-carboxylic acid and its pivaloylmethyl ester, or 7-[(Z)-2-(2-aminothiazol-4-yl)-2-hydroxyiminoacetamido]-3-[(Z)-2-(1,2,3-thiadiazol-5-yl)vinyl]-3-cephem-4-carboxylic acid.

* * * * *